US012569193B2

(12) United States Patent
Srivastava et al.

(10) Patent No.: US 12,569,193 B2
(45) Date of Patent: Mar. 10, 2026

(54) NEUROSTIMULATION PROGRAMMING AND TRIAGE BASED ON FREEFORM TEXT INPUTS

(71) Applicant: Boston Scientific Neuromodulation Corporation, Valencia, CA (US)

(72) Inventors: Kyle Harish Srivastava, Saint Paul, MN (US); Benjamin Phillip Hahn, Austin, TX (US); Amarpreet Singh Bains, Woodbury, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 516 days.

(21) Appl. No.: 18/075,670

(22) Filed: Dec. 6, 2022

(65) Prior Publication Data

US 2023/0181109 A1      Jun. 15, 2023

Related U.S. Application Data

(60) Provisional application No. 63/287,828, filed on Dec. 9, 2021.

(51) Int. Cl.
| | |
|---|---|
| *A61B 5/00* | (2006.01) |
| *A61N 1/36* | (2006.01) |

(Continued)

(52) U.S. Cl.
CPC .......... *A61B 5/4848* (2013.01); *A61B 5/4803* (2013.01); *A61N 1/36132* (2013.01);
(Continued)

(58) Field of Classification Search
CPC ........................... A61B 5/4848; A61B 5/4803; A61N 1/37264; A61N 1/36–3688; G06F 40/20;
(Continued)

(56) References Cited

U.S. PATENT DOCUMENTS

| | | | |
|---|---|---|---|
| 6,308,102 | B1 | 10/2001 | Sieracki et al. |
| 6,654,642 | B2 | 11/2003 | North et al. |

(Continued)

FOREIGN PATENT DOCUMENTS

WO      WO-2023107430 A1      6/2023

OTHER PUBLICATIONS

"Australian Application Serial No. 2022408043, First Examination Report mailed Feb. 27, 2025", 3 pgs.
(Continued)

*Primary Examiner* — Brian T Gedeon
(74) *Attorney, Agent, or Firm* — Schwegman Lundberg & Woessner, P.A.

(57) ABSTRACT

Systems and techniques are disclosed to evaluate a neurostimulation treatment provided from a neurostimulation device, based on freeform text analysis. In an example, a system or device to evaluate a neurostimulation treatment provided from a neurostimulation device is configured to perform operations that: obtain text content, originating from text or voice input of a human patient, which relates to a state of a human patient; identify a state of the human patient from natural language processing of the text content; obtain device data from the neurostimulation device; identify a state of the neurostimulation treatment of the human patient from the device data; associate the identified state of the human patient to the identified state of the neurostimulation treatment; and initiate an action for the neurostimulation treatment, based on the identified state of the human patient that is associated with the identified state of the neurostimulation treatment.

16 Claims, 12 Drawing Sheets

(51) Int. Cl.
  *A61N 1/372*       (2006.01)
  *G06F 40/20*       (2020.01)
  *G06F 40/30*       (2020.01)
(52) U.S. Cl.
  CPC ......... *A61N 1/37264* (2013.01); *G06F 40/20*
        (2020.01); *G06F 40/30* (2020.01)
(58) Field of Classification Search
  CPC ......... G06F 40/30; G06F 40/63; G16H 20/40;
        G16H 20/70; G16H 50/20; G16H 10/20
  See application file for complete search history.

(56)               References Cited

U.S. PATENT DOCUMENTS

|  |  |  |  |  |
|---|---|---|---|---|
| 8,983,615 | B2 | 3/2015 | Tahmasian et al. | |
| 10,733,266 | B2 | 8/2020 | Whitehurst | |
| 2004/0215286 | A1* | 10/2004 | Stypulkowski .... | A61N 1/36146 |
|  |  |  |  | 607/48 |
| 2014/0188457 | A1* | 7/2014 | Fink ........................ | G06F 40/30 |
|  |  |  |  | 704/9 |

| | | | |
|---|---|---|---|
| 2019/0110754 | A1 | 4/2019 | Rao et al. |
| 2019/0117978 | A1 | 4/2019 | Arcot Desai et al. |
| 2019/0358455 | A1* | 11/2019 | Lin ..................... A61N 1/36139 |
| 2021/0069512 | A1* | 3/2021 | Moffitt .................. G16H 50/20 |

OTHER PUBLICATIONS

"European Application Serial No. 22847179.3, Response to Communication pursuant to Rules 161 and 162 filed Jan. 16, 2025", 10 pgs.

"International Application Serial No. PCT/US2022/051934, International Preliminary Report on Patentability mailed Jun. 20, 2024", 9 pgs.

"International Application Serial No. PCT/US2022/051934, International Search Report mailed Mar. 21, 2023", 4 pgs.

"International Application Serial No. PCT/US2022/051934, Written Opinion mailed Mar. 21, 2023", 7 pgs.

Sheikhalishahi, Seyedmostafa, et al., "Natural Language Processing of Clinical Notes on Chronic Diseases: Systematic Review", Arxiv. org, Cornell University Library, 201 Olin Library Cornell University Ithaca, NY 14853, (Aug. 15, 2019), 18 pages.

* cited by examiner

_422_

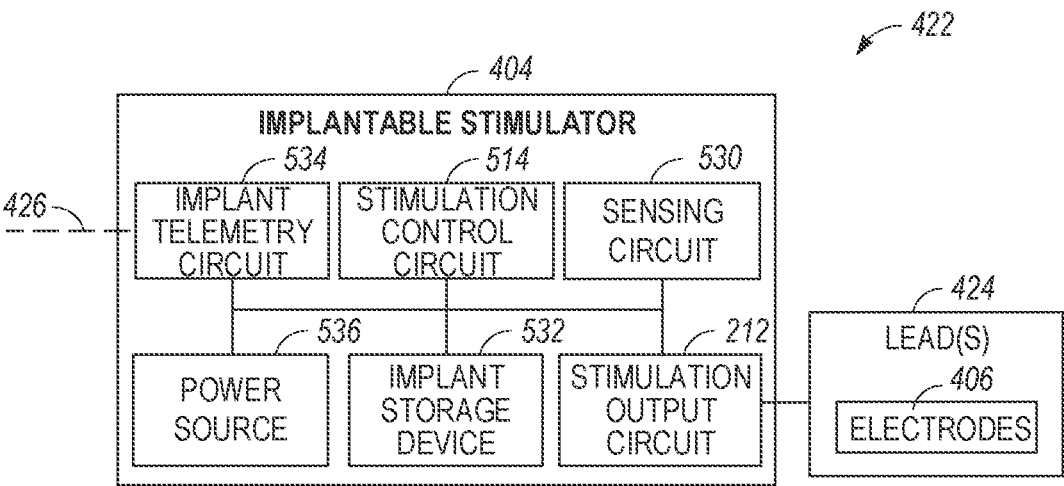

IMPLANTABLE STIMULATOR _404_

_534_ IMPLANT TELEMETRY CIRCUIT

_514_ STIMULATION CONTROL CIRCUIT

_530_ SENSING CIRCUIT

_426_

_536_ POWER SOURCE

_532_ IMPLANT STORAGE DEVICE

_212_ STIMULATION OUTPUT CIRCUIT

_424_ LEAD(S)

_406_ ELECTRODES

PROGRAMMING SYSTEM

_610_ USER INTERFACE

_612_ DISPLAY SCREEN

_614_ USER INPUT DEVICE

NEUROSTIMULATION PARAMETER SELECTION CIRCUIT

_622_

_620_ PROGRAMMING CONTROL CIRCUIT

_640_ EXTERNAL TELEMETRY CIRCUIT

_426_

_630_ CONTROLLER

_616_ EXTERNAL STORAGE DEVICE

_618_ EXTERNAL COMMUNICATION DEVICE

_650_ DATA ANALYSIS SYSTEM

_660_ TREATMENT ACTION CIRCUITRY

_662_ PATIENT OUTPUT CIRCUITRY

_664_ CLINICIAN OUTPUT CIRCUITRY

_652_ DEVICE DATA PROCESSING CIRCUIT

_654_ TEXT PROCESSING CIRCUIT

_656_ STORAGE DEVICE

FIG. 6

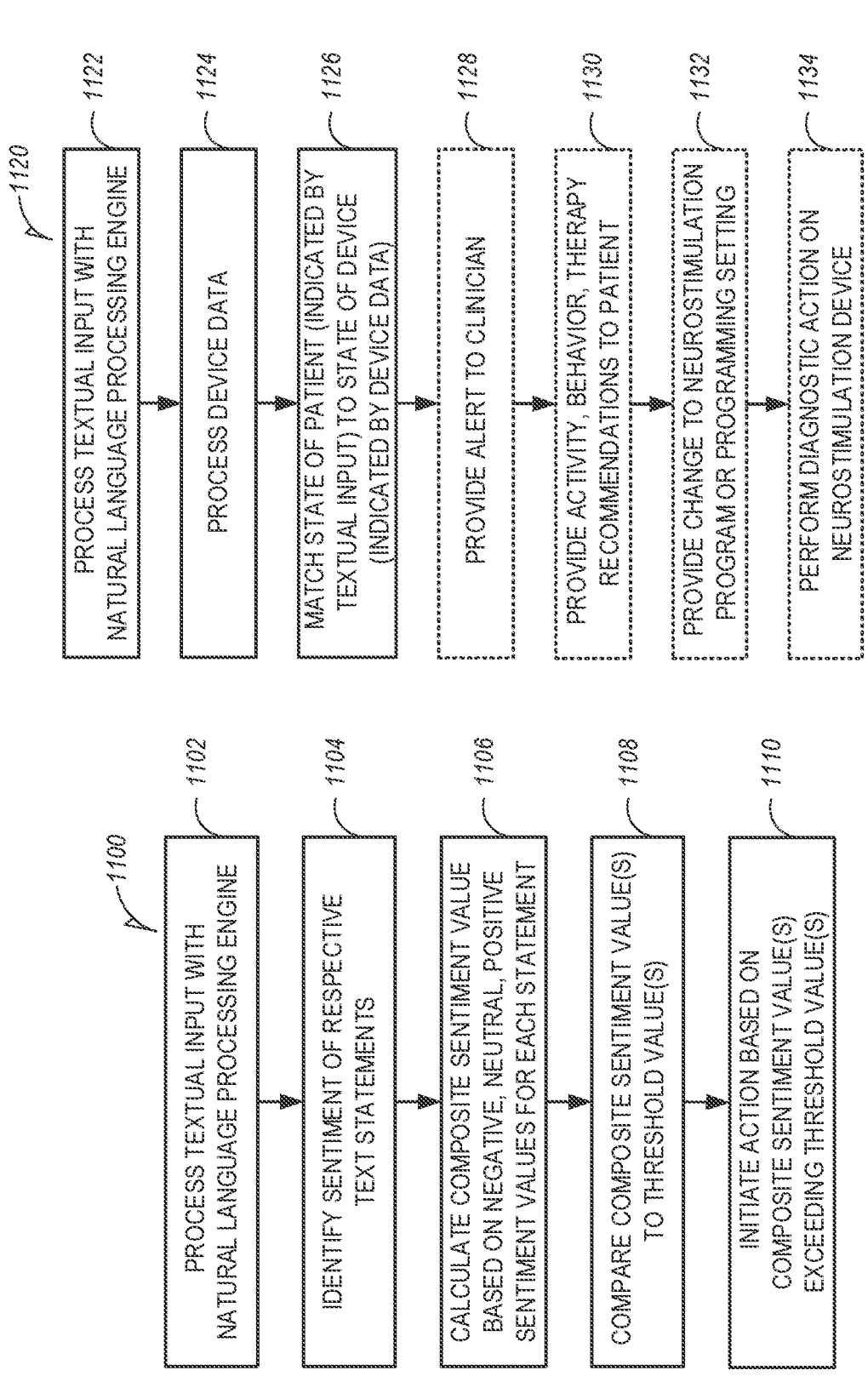

1120

1122 PROCESS TEXTUAL INPUT WITH NATURAL LANGUAGE PROCESSING ENGINE

1124 PROCESS DEVICE DATA

1126 MATCH STATE OF PATIENT (INDICATED BY TEXTUAL INPUT) TO STATE OF DEVICE (INDICATED BY DEVICE DATA)

1128 PROVIDE ALERT TO CLINICIAN

1130 PROVIDE ACTIVITY, BEHAVIOR, THERAPY RECOMMENDATIONS TO PATIENT

1132 PROVIDE CHANGE TO NEUROSTIMULATION PROGRAM OR PROGRAMING SETTING

1134 PERFORM DIAGNOSTIC ACTION ON NEUROSTIMULATION DEVICE

1102 PROCESS TEXTUAL INPUT WITH NATURAL LANGUAGE PROCESSING ENGINE

1104 IDENTIFY SENTIMENT OF RESPECTIVE TEXT STATEMENTS

1106 CALCULATE COMPOSITE SENTIMENT VALUE BASED ON NEGATIVE, NEUTRAL, POSITIVE SENTIMENT VALUES FOR EACH STATEMENT

1108 COMPARE COMPOSITE SENTIMENT VALUE(S) TO THRESHOLD VALUE(S)

1110 INITIATE ACTION BASED ON COMPOSITE SENTIMENT VALUE(S) EXCEEDING THRESHOLD VALUE(S)

FIG. 11A

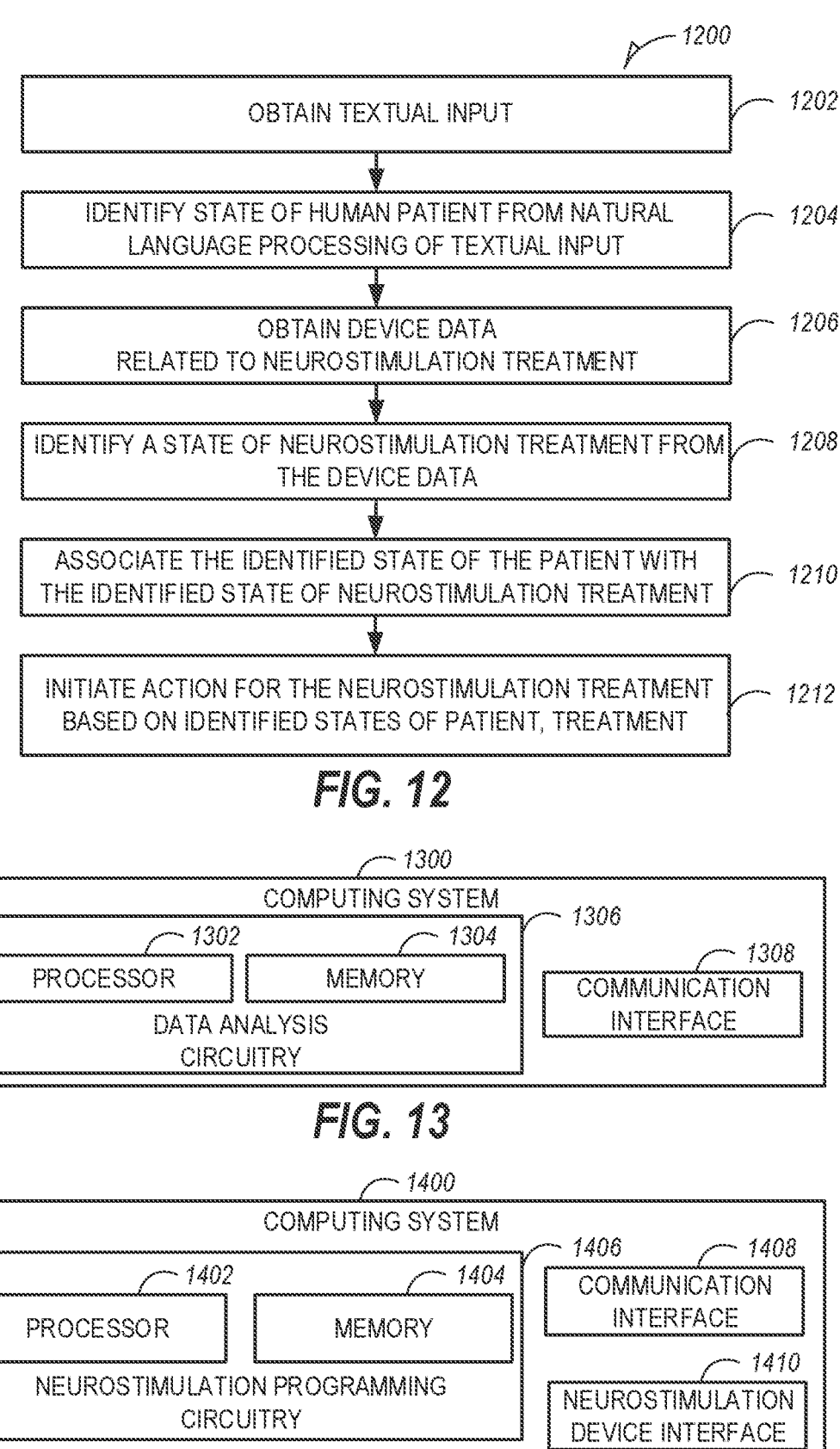

*1200*

OBTAIN TEXTUAL INPUT — *1202*

IDENTIFY STATE OF HUMAN PATIENT FROM NATURAL LANGUAGE PROCESSING OF TEXTUAL INPUT — *1204*

OBTAIN DEVICE DATA RELATED TO NEUROSTIMULATION TREATMENT — *1206*

IDENTIFY A STATE OF NEUROSTIMULATION TREATMENT FROM THE DEVICE DATA — *1208*

ASSOCIATE THE IDENTIFIED STATE OF THE PATIENT WITH THE IDENTIFIED STATE OF NEUROSTIMULATION TREATMENT — *1210*

INITIATE ACTION FOR THE NEUROSTIMULATION TREATMENT BASED ON IDENTIFIED STATES OF PATIENT, TREATMENT — *1212*

COMPUTING SYSTEM

*1302* PROCESSOR    *1304* MEMORY

DATA ANALYSIS CIRCUITRY

*1306* *1308* COMMUNICATION INTERFACE

COMPUTING SYSTEM

*1402* PROCESSOR    *1404* MEMORY

NEUROSTIMULATION PROGRAMMING CIRCUITRY

*1406* *1408* COMMUNICATION INTERFACE

*1410* NEUROSTIMULATION DEVICE INTERFACE

*FIG. 14*

NEUROSTIMULATION PROGRAMMING AND TRIAGE BASED ON FREEFORM TEXT INPUTS

CLAIM OF PRIORITY

This application claims the benefit of U.S. Provisional Application No. 63/287,828, filed on Dec. 9, 2021, which is hereby incorporated by reference in its entirety.

TECHNICAL FIELD

The present disclosure relates generally to medical devices, and more particularly, to systems, devices, and methods for electrical stimulation programming using various approaches determined from freeform text processing and user inputs, including to determine programming values, assess patient or device conditions, perform device diagnostics, or recommend outcomes for implanted electrical stimulation for pain treatment and/or management.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system.

A neurostimulation system can be used to electrically stimulate tissue or nerve centers to treat nervous or muscular disorders. For example, an SCS system may be configured to deliver electrical pulses to a specified region of a patient's spinal cord, such as particular spinal nerve roots or nerve bundles, to produce an analgesic effect that masks pain sensation, or to produce a functional effect that allows increased movement or activity of the patient. Other forms of neurostimulation may include a DBS system which uses similar pulses of electricity at particular locations in the brain to reduce symptoms of essential tremors, Parkinson's disease, psychological disorders, or the like.

While modern electronics can accommodate the need for generating and delivering neurostimulation energy in a variety of forms, the capability of a neurostimulation system depends on its post-manufacturing programmability to a great extent. One limiting factor for applications of neurostimulation therapies is that, even if a number of advanced programs can be applied by a neurostimulation device, there is often a delay for implementing new or improved neurostimulation treatments. Such a delay may be due to the infrequency of care provided by a clinician or other medical professional who oversees the treatment, and a lack of clear information regarding the results of the treatment.

Various approaches for neurostimulation programming and customization have attempted more dynamic forms of open-loop and closed-loop programing, to allow new neurostimulation parameters or programs to be introduced, deployed, tested, and adjusted by a clinician or the subject patient. Although some neurostimulation devices provide the capability to enable a patient to switch between programs or change the level of a certain stimulation effect, it is often unclear whether such changes (or, which changes) are beneficial to a patient and result in improvement to the patient's medical condition.

SUMMARY

The following Summary provides examples as an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

Example 1 is a system (e.g., a programmed computer system, a neuromodulation programming system, etc.) to evaluate a neurostimulation treatment provided from a neurostimulation device (e.g., an implantable neurostimulation device), the system comprising: at least one processor (e.g., processing circuitry); and at least one memory device (e.g., volatile or non-volatile memory circuitry or units) comprising instructions, which when executed by the processor, cause the processor to perform operations (e.g., method operations) that: obtain text content relating to a state of a human patient, the text content originating from input of the human patient; identify a state of the human patient from natural language processing of the text content; obtain device data from the neurostimulation device, the neurostimulation device being used for neurostimulation treatment of the human patient; identify a state of the neurostimulation treatment of the human patient from the device data; associate the identified state of the human patient to the identified state of the neurostimulation treatment; and initiate an action for the neurostimulation treatment, based on the identified state of the human patient that is associated with the identified state of the neurostimulation treatment.

In Example 2, the subject matter of Example 1 optionally includes subject matter where the operations to identify the state of the human patient include operations to: identify a sentiment of at least one statement provided in the text content, using the natural language processing, wherein the state of the human patient is determined using the sentiment of the at least one statement.

In Example 3, the subject matter of Example 2 optionally includes subject matter where the sentiment of the at least one statement comprises a calculated sentiment value that is compared with a threshold sentiment value, and wherein the action for the neurostimulation treatment is initiated based on the calculated sentiment value exceeding the threshold sentiment value.

In Example 4, the subject matter of Example 3 optionally includes subject matter where the calculated sentiment value is produced from a negative sentiment value, a neutral sentiment value, and a positive sentiment value that is calculated for each of the at least one statement.

In Example 5, the subject matter of any one or more of Examples 2-4 optionally include subject matter where the state of the human patient comprises at least one physiological condition identified using the natural language processing, wherein the at least one physiological condition relates to: pain, sleep, movement, medication, or emotional state of the human patient, and wherein the state of the neurostimulation treatment comprises at least one device condition identified from the device data, wherein the at least one device condition relates to: power status, program usage, battery level, impedance, device settings, or scheduled cycles, for the neurostimulation device.

In Example 6, the subject matter of any one or more of Examples 1-5 optionally include subject matter where operations to associate the identified state of the human patient to the identified state of the neurostimulation treatment comprise operations to: match use of at least one neurostimulation program to the identified state of the human patient, the at least one neurostimulation program used by the neurostimulation device.

In Example 7, the subject matter of Example 6 optionally includes subject matter where the use of the at least one neurostimulation program is identified based on a time of the use of the at least one neurostimulation program, matched to at least one time associated with the identified state of the human patient.

In Example 8, the subject matter of any one or more of Examples 1-7 optionally include subject matter where the text content originates from at least one of: a text chat session conducted between a chatbot and the human patient; a voice chat session conducted between a virtual agent and the human patient, with at least a portion of the voice chat session converted to text; a text message session conducted between a text service and the human patient; an audio recording of a discussion conducted between the human patient and a human agent, with at least a portion of the audio recording converted to text; or a freeform text input provided by the human patient.

In Example 9, the subject matter of any one or more of Examples 1-8 optionally include subject matter where the initiated action comprises operations to provide an alert to a clinician or a customer assistance entity associated with the neurostimulation treatment of the human patient, the alert to provide information for the identified state of the human patient and the identified state of the neurostimulation treatment.

In Example 10, the subject matter of any one or more of Examples 1-9 optionally include subject matter where the initiated action comprises operations to perform a diagnostic action on the neurostimulation device.

In Example 11, the subject matter of any one or more of Examples 1-10 optionally include subject matter where the initiated action comprises operations to provide activity, behavior, or therapy recommendations to the human patient.

In Example 12, the subject matter of any one or more of Examples 1-11 optionally include subject matter where the initiated action comprises operations to change or offer a change to a neurostimulation programming setting on the neurostimulation device, the neurostimulation programming setting associated with the neurostimulation treatment of the human patient.

In Example 13, the subject matter of Example 12 optionally includes subject matter where the change to the neurostimulation programming setting comprises operations to: identify programming values for at least one neurostimulation programming parameter in the neurostimulation program based on the identified state of the human patient that is associated to the identified state of the neurostimulation treatment; wherein the identified programming values specify a change in operation of the neurostimulation program for one or more of: pulse patterns, pulse shapes, a spatial location of pulses, waveform shapes, or a spatial location of waveform shapes, for modulated energy provided with a plurality of leads of the neurostimulation device.

Example 14 is a machine-readable medium including instructions, which when executed by a machine, cause the machine to perform the operations of the system of any of the Examples 1 to 13.

Example 15 is a method to perform the operations of the system of any of the Examples 1 to 13.

Example 16 is a device for use to evaluate a neurostimulation treatment provided from a neurostimulation device, the device comprising: at least one processor and at least one memory; data processing circuitry, operable with the processor and the memory, the data processing circuitry configured to: receive device data from the neurostimulation device, the neurostimulation device being used for neurostimulation treatment of a human patient; and identify a state of the neurostimulation treatment of the human patient from the device data; text processing circuitry, operable with the processor and the memory, the text processing circuitry configured to: receive text content relating to a state of the human patient, the text content originating from input of the human patient; and identify a state of the human patient from natural language processing of the text content; and neurostimulation treatment evaluation circuitry, in operation with the at least one processor and the at least one memory, configured to: associate the identified state of the human patient to the identified state of the neurostimulation treatment; and initiate an action for the neurostimulation treatment, based on the identified state of the human patient that is associated with the identified state of the neurostimulation treatment.

In Example 17, the subject matter of Example 16 optionally includes subject matter where the operations to identify the state of the human patient include operations to: identify a sentiment of at least one statement provided in the text content, using the natural language processing, wherein the state of the human patient is determined using the sentiment of the at least one statement.

In Example 18, the subject matter of Example 17 optionally includes subject matter where the sentiment of the at least one statement comprises a calculated sentiment value that is compared with a threshold sentiment value, and wherein the action for the neurostimulation treatment is initiated based on the calculated sentiment value exceeding the threshold sentiment value.

In Example 19, the subject matter of Example 18 optionally includes subject matter where the calculated sentiment value is produced from a negative sentiment value, a neutral sentiment value, and a positive sentiment value that is calculated for each of the at least one statement.

In Example 20, the subject matter of any one or more of Examples 17-19 optionally include subject matter where the state of the human patient comprises at least one physiological condition identified using the natural language processing, wherein the at least one physiological condition relates to: pain, sleep, movement, medication, or emotional state, of the human patient, and wherein the state of the neurostimulation treatment comprises at least one device condition identified from the device data, wherein the at least one device condition relates to: power status, program usage, battery level, impedance, device settings, or scheduled cycles, for the neurostimulation device.

In Example 21, the subject matter of any one or more of Examples 16-20 optionally include subject matter where operations to associate the identified state of the human patient to the identified state of the neurostimulation treatment comprise operations to: match use of at least one neurostimulation program to the identified state of the human patient, the at least one neurostimulation program used by the neurostimulation device.

In Example 22, the subject matter of Example 21 optionally includes subject matter where the use of the at least one neurostimulation program is identified based on a time of the use of the at least one neurostimulation program, matched to at least one time associated with the identified state of the human patient.

In Example 23, the subject matter of any one or more of Examples 16-22 optionally include subject matter where the text content originates from at least one of: a text chat session conducted between a chatbot and the human patient; a voice chat session conducted between a virtual agent and the human patient, with at least a portion of the voice chat session converted to text; a text message session conducted between a text service and the human patient; an audio recording of a discussion conducted between the human patient and a human agent, with at least a portion of the audio recording converted to text; or a freeform text input provided by the human patient.

In Example 24, the subject matter of any one or more of Examples 16-23 optionally include subject matter where the initiated action comprises operations to: provide an alert to a clinician or a customer assistance entity associated with the neurostimulation treatment of the human patient, the alert to provide information for the identified state of the human patient and the identified state of the neurostimulation treatment; perform a diagnostic action on the neurostimulation device; or provide activity, behavior, or therapy recommendations to the human patient.

In Example 25, the subject matter of any one or more of Examples 16-24 optionally include subject matter where the initiated action comprises operations to: change or offer a change to a neurostimulation programming setting on the neurostimulation device, the neurostimulation programming setting associated with the neurostimulation treatment of the human patient; wherein the change to the neurostimulation programming setting comprises operations to identify programming values for at least one neurostimulation programming parameter in the neurostimulation program based on the identified state of the human patient that is associated to the identified state of the neurostimulation treatment; and wherein the identified programming values specify a change in operation of the neurostimulation program for one or more of: pulse patterns, pulse shapes, a spatial location of pulses, waveform shapes, or a spatial location of waveform shapes, for modulated energy provided with a plurality of leads of the neurostimulation device.

Example 26 is a method for use to evaluate a neurostimulation treatment provided from a neurostimulation device, the method comprising a plurality of operations executed with at least one processor of an electronic device, the plurality of operations comprising: obtaining text content relating to a state of a human patient, the text content originating from input of the human patient; identifying a state of the human patient from natural language processing of the text content; obtaining device data from the neurostimulation device, the neurostimulation device being used for neurostimulation treatment of the human patient; identifying a state of the neurostimulation treatment of the human patient from the device data; associating the identified state of the human patient to the identified state of the neurostimulation treatment; and initiating an action for the neurostimulation treatment, based on the identified state of the human patient that is associated with the identified state of the neurostimulation treatment.

In Example 27, the subject matter of Example 26 optionally includes subject matter where identifying the state of the human patient comprises: identifying a sentiment of at least one statement provided in the text content, using the natural language processing, wherein the state of the human patient is determined using the sentiment of the at least one statement.

In Example 28, the subject matter of Example 27 optionally includes subject matter where the sentiment of the at least one statement comprises a calculated sentiment value that is compared with a threshold sentiment value, and wherein the action for the neurostimulation treatment is initiated based on the calculated sentiment value exceeding the threshold sentiment value.

In Example 29, the subject matter of Example 28 optionally includes subject matter where the calculated sentiment value is produced from a negative sentiment value, a neutral sentiment value, and a positive sentiment value that is calculated for each of the at least one statement.

In Example 30, the subject matter of any one or more of Examples 27-29 optionally include subject matter where the state of the human patient comprises at least one physiological condition identified using the natural language processing, wherein the at least one physiological condition relates to: pain, sleep, movement, medication, or emotional state, of the human patient, and wherein the state of the neurostimulation treatment comprises at least one device condition identified from the device data, wherein the at least one device condition relates to: power status, program usage, battery level, impedance, device settings, or scheduled cycles, for the neurostimulation device.

In Example 31, the subject matter of any one or more of Examples 26-30 optionally include subject matter where associating the identified state of the human patient to the identified state of the neurostimulation treatment comprises: matching use of at least one neurostimulation program to the identified state of the human patient, the at least one neurostimulation program used by the neurostimulation device.

In Example 32, the subject matter of Example 31 optionally includes subject matter where the use of the at least one neurostimulation program is identified based on a time of the use of the at least one neurostimulation program, matched to at least one time associated with the identified state of the human patient.

In Example 33, the subject matter of any one or more of Examples 26-32 optionally include subject matter where the text content originates from at least one of: a text chat session conducted between a chatbot and the human patient; a voice chat session conducted between a virtual agent and the human patient, with at least a portion of the voice chat session converted to text; a text message session conducted between a text service and the human patient; an audio recording of a discussion conducted between the human patient and a human agent, with at least a portion of the audio recording converted to text; or a freeform text input provided by the human patient.

In Example 34, the subject matter of any one or more of Examples 26-33 optionally include subject matter where the initiated action comprises: providing an alert to a clinician or a customer assistance entity associated with the neurostimulation treatment of the human patient, the alert to provide information for the identified state of the human patient and the identified state of the neurostimulation treatment; performing a diagnostic action on the neurostimulation device; or providing activity, behavior, or therapy recommendations to the human patient.

In Example 35, the subject matter of any one or more of Examples 26-34 optionally include subject matter where the initiated action comprises operations to: implementing a change or offering a change to a neurostimulation programming setting on the neurostimulation device, the neurostimulation programming setting associated with the neurostimulation treatment of the human patient; wherein the change to the neurostimulation programming setting comprises identifying programming values for at least one neurostimulation programming parameter in the neurostimulation program based on the identified state of the human patient that is associated to the identified state of the neurostimulation treatment; and wherein the identified programming values specify a change in operation of the neurostimulation program for one or more of: pulse patterns, pulse shapes, a spatial location of pulses, waveform shapes, or a spatial location of waveform shapes, for modulated energy provided with a plurality of leads of the neurostimulation device.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 5 illustrates, by way of example, an embodiment of an implantable stimulator and one or more leads of a neurostimulation system, such as the implantable neurostimulation system of FIG. 4.

FIG. 6 illustrates, by way of example, an embodiment of a programming system and data analysis system for use with a neurostimulation system, such as the implantable neurostimulation system of FIG. 4.

FIGS. 11A and 11B illustrate, by way of example, flowchart sequences of evaluation of textual input by a natural language processing engine and resulting actions from such evaluations.

FIG. 12 illustrates, by way of example, a flowchart of a method implemented by a system or device to evaluate a neurostimulation treatment provided from a neurostimulation device based on evaluated input text.

FIG. 13 illustrates, by way of example, a block diagram of an embodiment of a computing system implementing freeform text or related device data analysis to monitor, modify, or effect operation and output of a neurostimulation programming mode.

FIG. 14 illustrates, by way of example, a block diagram of an embodiment of a computing system implementing neurostimulation programming circuitry, to cause programming of an implantable electrical neurostimulation device.

DETAILED DESCRIPTION

Figure 1:
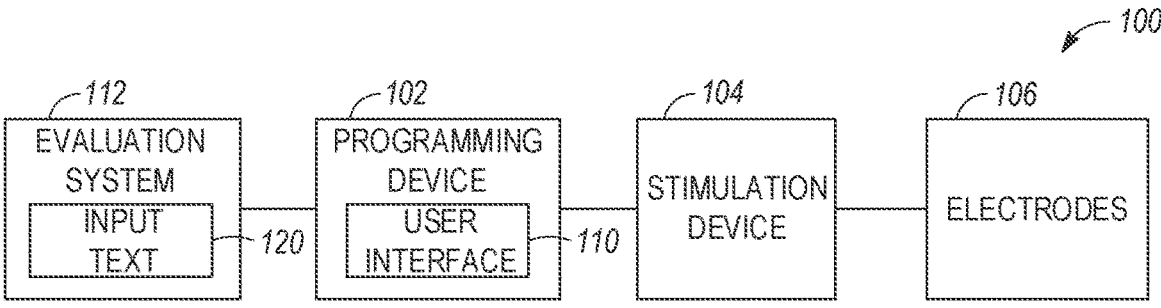
FIG. 1 illustrates, by way of example, an embodiment of a neurostimulation system.

This document discusses various techniques that can generate, determine, or monitor programming values or treatment effects of an implantable electrical neurostimulation device, in connection with the treatment of pain or related physiological conditions in a human subject (e.g., a patient). As an example, various systems and methods are described to generate, identify, implement, adjust, or assess parameters of neurostimulation treatment and treatment effects, based on the evaluation of patient freeform text and similar forms of unstructured or unclassified data. These systems and methods are further designed to evaluate the current results of neurostimulation treatment, and to determine changes or actions relative to therapy objectives and desired outcomes. As a result, programming modifications, alerts, or other outcomes may be achieved to assist the treatment for a particular patient.

In many existing approaches of neurostimulation treatment involving clinician-based programming, a patient ends up needing to provide detailed feedback to a clinician (often, in a clinical setting such as during a scheduled doctor's visit) before a treatment issue can be identified and changes can be implemented to neurostimulation treatment. Even simple clinician queries such as, "Does the neurostimulation effectively treat your pain?" may be difficult for a patient to answer, especially when evaluating a course of treatment over time that involves multiple stimulation programs. The present techniques and systems improve this and related scenarios through the analysis of ongoing feedback, obtained directly from the patient, using textual analysis and other analytical methods.

In various examples, natural language processing is used to analyze freeform text that is input from a patient undergoing neurostimulation treatment. This textual analysis is used to produce scores which can measure polarity or valence (i.e., the degree to which some outcome is "good" (positive valence) or "bad" (negative valence)). Scores produced from text may be used to then identify which device settings, programs, parameters, or operations are effective, ineffective, or problematic. Such information also may be used to generate alerts, reports, or aspects of open-loop and closed-loop programming modifications.

In addition to use with aspects of programs and programming values, information from the evaluation of freeform text may also be used to cause device actions (e.g., to run diagnostics on the neurostimulation device). In still other examples, information from the evaluation of freeform text may also be used to provide informational content to a patient or to a clinician (e.g., to present guidance regarding the effects of treatment or ways to improve treatment outcomes), to provide a clinical triage system, or to update data records, among other effects.

In various embodiments, the present subject matter may be implemented using a combination of hardware and software designed to capture and analyze freeform text or other unstructured information from users, and related device data or context from a neurostimulation treatment. For instance, some examples are provided with reference to a mobile computing device (e.g., smartphone) app executing a user interface to collect freeform text, entered in the form of questions. Other examples are provided with reference to a computing system implemented via a chatbot (e.g., generating data for a smartphone app chat session or SMS message chat session) that presents questions or replies, in an effort to collect and process patient input provided in text (e.g., provided directly in freeform text from a patient response, provided from converted voice-to-text responses, or provided directly or indirectly with other interactions with various parties or entities). Still other examples are provided with reference to a computing system platform which captures and evaluates data from sensors (e.g., wearable devices, implantable devices, or the neurostimulation device) that can be used to cross-reference or correlate freeform text statements from a patient. Many of the following approaches are provided with specific reference to text analysis and natural language processing, but it will be understood that such approaches may be supplemented or substituted with other technical implementations of text processing and data analysis involving including artificial intelligence (AI), including models implementing machine learning, neural networks, decision trees, and the like.

It will be understood that a variety of the following embodiments may be operated to provide users such as patients, caregivers, clinicians, researchers, physicians, or others with the ability to monitor, collect and provide feedback, and adapt neurostimulation programs and neurostimulation effects (including, neurostimulation programming that provides a variation in the location, intensity, and type of defined waveforms and patterns in an effort to increase therapeutic efficacy and/or patient satisfaction). While neurostimulation therapies, such as SCS and DBS therapies, are specifically discussed as examples, the present subject matter may apply to other therapies that employs stimulation pulses of electrical or other forms of energy for treating chronic pain or like physiological or psychological conditions.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc. Accordingly, the following drawings provide an introduction to the features of an example neurostimulation system and how such programming may be accomplished through open-loop or closed-loop neurostimulation systems, and integrated with the present data analysis platforms.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are selected or programmable by a clinical user, such as a physician or other caregiver who treats the patient using system 100; however, some of the parameters may also be provided in connection with closed-loop programming logic and adjustment Programming device 102 provides the user with accessibility to implement, change, or modify the programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. These adjustments may also include changing and editing values for the user-programmable parameters or sets of the user-programmable parameters individually (including values set in response to a therapy efficacy indication). Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

The present approaches further provide examples of an evaluation system 112, such as a data analysis system, that is used to adapt, modify, start, stop, monitor, or identify a neurostimulation treatment with stimulation device 104. This evaluation system 112 initiates an action related to the neurostimulation treatment based on text analysis performed on input text 120. This input text 120 may be directly collected from the patient and analyzed by the evaluation system 112, to then cause a programming effect in the programming device 102, and the stimulation device 104, and the neurostimulation treatment provided by the electrodes 106.

As described in more detail below with respect to the data flows in FIGS. 7 to 12, a user, e.g., the patient, can provide text inputs to the evaluation system 112, which are used to select, load, modify, implement, measure, analyze, or evaluate one or more parameters of a defined program for neurostimulation treatment that is implemented by the stimulation device 104, or the operation of the stimulation device 104. This evaluation may be based on a combination of natural language processing, sentiment analysis, rules, and other operational or treatment objectives that are identified. Various logic or algorithms can then determine an appropriate action to take based on the state of the patient, including but not limited to: a program or parameter change or recommendation to produce an improvement for a treatment objective (such as to address pain, increase mobility, reduce sleep disruption, and the like); diagnostic or remedial actions on the stimulation device 104; data logging or alerts to the patient or a clinician associated with the patient; and the like.

Example parameters that can be implemented by a selected neurostimulation program include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time). As detailed in FIG. 6, a controller, e.g., controller 630 of FIG. 6, can implement program(s) and parameter setting(s) to affect a specific neurostimulation waveform, pattern, or energy output, using a program or setting in storage, e.g., external storage device 616 of FIG. 6, or using settings communicated via an external communication device 618 of FIG. 6 corresponding to the selected program. The implementation of such program(s) or setting(s) may further define a therapy strength and treatment type corresponding to a specific pulse group, or a specific group of pulse groups, based on the specific programs or settings. The evaluation system 112 and the evaluation of the input text 120 provides a mechanism to determine the effectiveness of such programs or settings, and to identify issues and provide remediation for ineffective programs or settings, offer suggestions or recommendations for new programs or settings, or even to automatically change programs or settings.

Portions of the evaluation system 112, the stimulation device 104 (e.g., implantable medical device), or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could also include a subcutaneous medical device (e.g., subcutaneous ICD, subcutaneous diagnostic device), wearable medical devices (e.g., patch-based sensing device), or other external medical devices.

Figure 2:
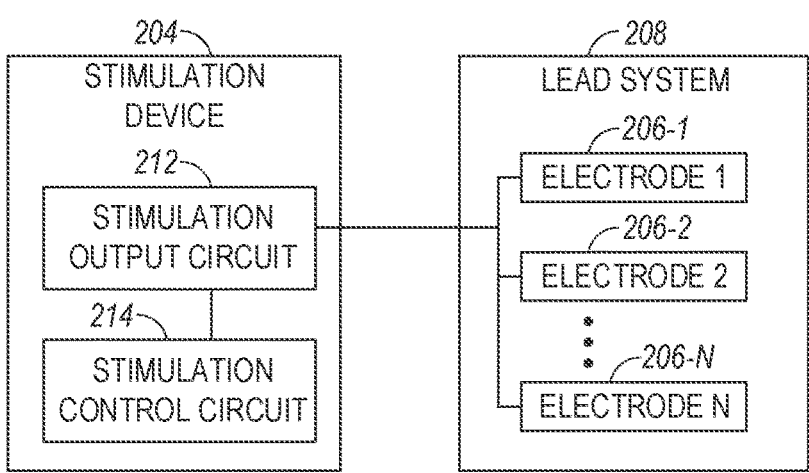
FIG. 2 illustrates, by way of example, an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power. The neurostimulation system 100 may also integrate with other sensors, or such other sensors may independently provide information for use with programming of the neurostimulation system 100.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a huge selection of available modulation parameter sets to the clinician or patient. For example, if the neurostimulation system to be programmed has sixteen electrodes, millions of modulation parameter value combinations may be available for programming into the neurostimulation system. Furthermore, some SCS systems have as many as thirty-two electrodes, which exponentially increases the number of modulation parameter value combinations available for programming.

Figure 3:
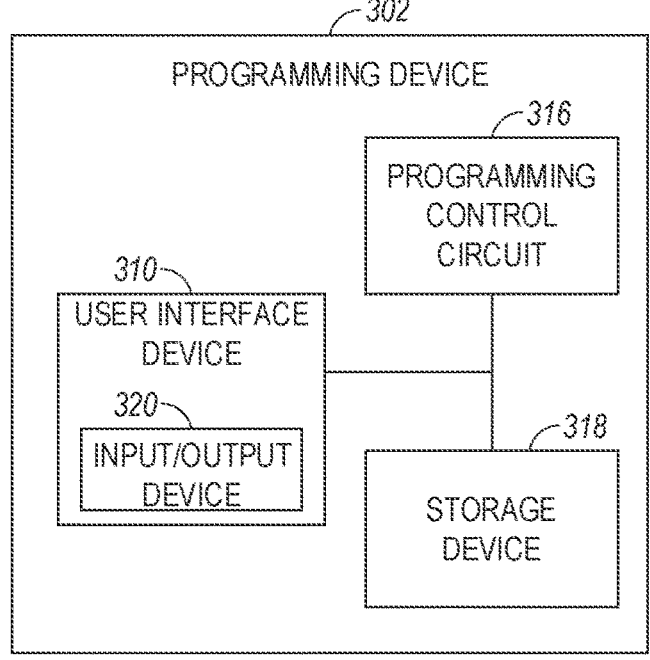
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), or other graphical input/output relating to therapy objectives, efficacy of applied treatment, user feedback, and the like. In various examples, the user interface device 310 can receive user input to initiate or control the implementation of the programs or program changes which are recommended, modified, selected, or loaded through use of an open or closed loop programming system, including those driven by freeform text analysis as discussed herein.

In various embodiments, the input/output device 320 allows the patient user to apply, change, modify, or discontinue certain building blocks of a program and a frequency at which a selected program is delivered. In various embodiments, the input/output device 320 can allow the patient user to save, retrieve, and modify programs (and program settings) loaded from a clinical encounter, managed from the patient feedback computing device, or stored in storage device 318 as templates. In various embodiments, the input/output device 320 and accompanying software on the user interface device 310 allows newly created building blocks, program components, programs, and program modifications to be saved, stored, or otherwise persisted in storage device 318. Thus, it will be understood that the user interface device 310 may allow many forms of device operation and control, even if closed loop programming is occurring. The analysis of freeform text, discussed herein, may be in addition to (or in place of) this user input and other forms of closed-loop or open-loop programming.

In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs. Thus, the input/output device 320 may include one or more of a touchscreen, keyboard, keypad, touchpad, trackball, joystick, and mouse. The logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
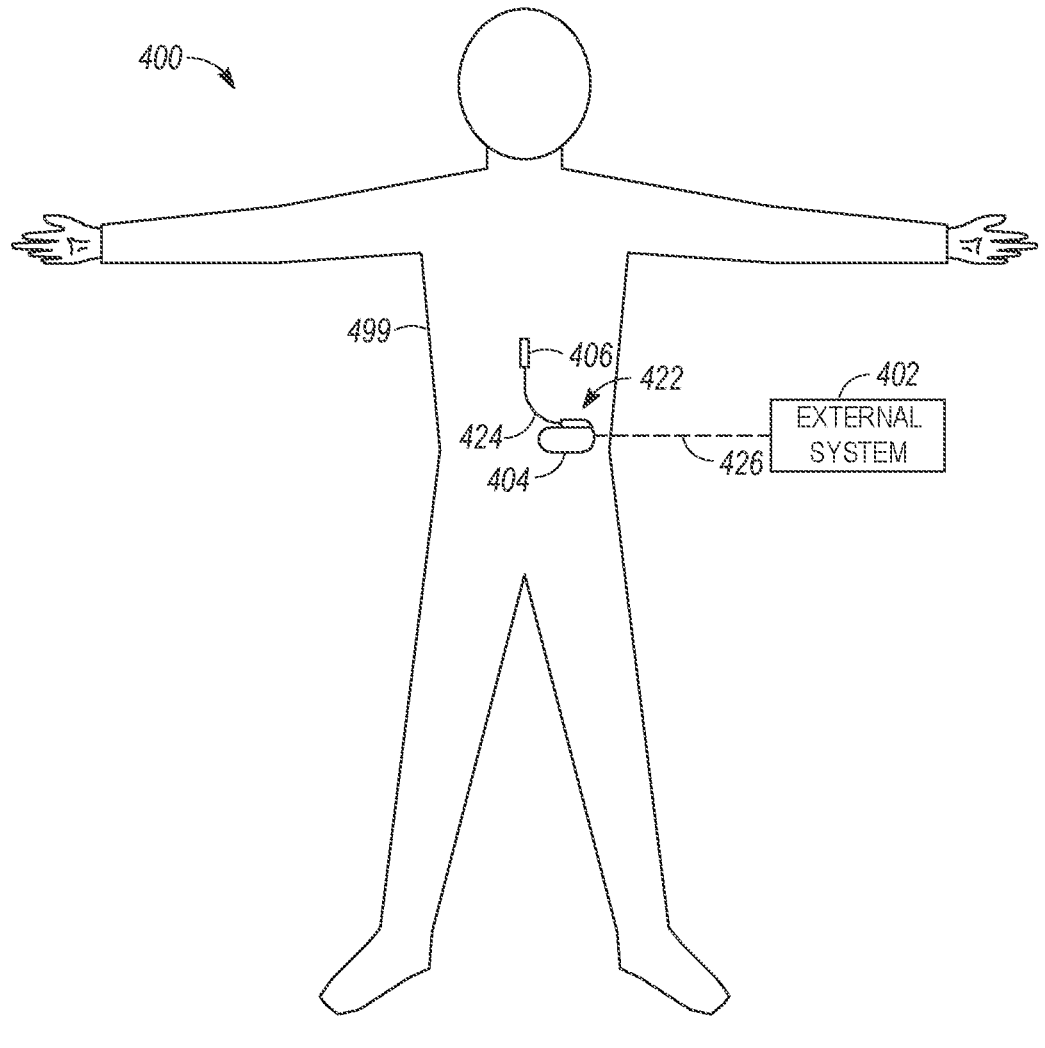
FIG. 4 illustrates, by way of example, an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, collected from other sensors or devices (not shown), or manually obtained from user input entered in a user interface (such as with the user input scenarios discussed below). Such feedback and other information may comprise the device data evaluated as part of association and matching with freeform text input.

As used herein, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuro-plasticity or neuro-genesis of tissue. It will be understood that other clinical effects and physiological mechanisms may also be provided through use of such stimulation techniques.

FIG. 5 illustrates an embodiment of the implantable stimulator 404 and the one or more leads 424 of an implantable neurostimulation system, such as the implantable system 422. The implantable stimulator 404 may include a sensing circuit 530 used for an optional sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation, including in the closed loop programming processes discussed herein. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program selected with the closed-loop programming system) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs which are activated, de-activated, or modified using the approaches discussed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530, the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of a programming system 602 used as part of an implantable neurostimulation system, such as the external system 402, with the programming system 602 configured to send and receive device data (e.g., commands, parameters, program selections, information). FIG. 6 also illustrates an embodiment of a data analysis computing system 650, communicatively coupled to the programming system 602, with the data analysis computing system 650 used to perform data analysis on freeform text and device data in connection with neurostimulation treatment by the implantable neurostimulation system.

The programming system 602 represents an embodiment of the programming device 302, and includes an external telemetry circuit 640, an external storage device 616, a programming control circuit 620, a user interface device 610, a controller 630, and an external communication device 618, to effect programming of a connected neurostimulation device. The operation of the neurostimulation parameter selection circuit 622 enables selection, modification, and implementation of a particular set of parameters or settings for neurostimulation programming. The particular set of parameters or settings that are selected, modified, or implemented may be based on freeform text analysis, such as discussed with reference to the text analysis and data evaluation performed with functions described in FIGS. 7 to 10, below.

The external telemetry circuit 640 provides the closed loop programming system 602 with wireless communication to and from another controllable device such as the implantable stimulator 404 via the telemetry link 426, including transmitting one or a plurality of stimulation parameters (including selected, identified, or modified stimulation parameters of a selected program) to the implantable stimulator 404. In one embodiment, the external telemetry circuit 640 also transmits power to the implantable stimulator 404 through inductive coupling.

The external communication device 618 may provide a mechanism to conduct communications with a programming information source, such as a data service, program modeling system, to receive program information, settings and values, models, functionality controls, or the like, via an external communication link (not shown). In a specific example, the external communication device 618 communicates with the data analysis computing system 650 to obtain commands or instructions in connection with parameters or settings that are selected, modified, or implemented based on freeform text analysis from the data analysis computing system 650. The external communication device 618 may communicate using any number of wired or wireless communication mechanisms described in this document, including but not limited to IEEE 802.11 (Wi-Fi), Bluetooth, Infrared, and like standardized and proprietary wireless communications implementations. Although the external telemetry circuit 640 and the external communication device 618 are depicted as separate components within the closed-loop programming system 602, the functionality of both of these components may be integrated into a single communication chipset, circuitry, or device.

The external storage device 616 stores a plurality of existing neurostimulation waveforms, including definable waveforms for use as a portion of the pattern of the neurostimulation pulses, settings and setting values, other portions of a program, and related treatment efficacy indication values. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 616 can be definable at least in part by one or more parameters including, but not limited to the following: amplitude, pulse width, frequency, duration (s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 616 may also store a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program may be correlated to the control of these waveforms and definable fields.

The programming control circuit 620 represents an embodiment of a programming control circuit 316 and may translate or generate the specific stimulation parameters or changes which are to be transmitted to the implantable stimulator 404, based on the results of the neurostimulation parameter selection circuit 622. The pattern may be defined using one or more waveforms selected from the plurality of individually definable waveforms (e.g., defined by a program) stored in an external storage device 616. In various embodiments, the programming control circuit 620 checks values of the plurality of stimulation parameters against safety rules to limit these values within constraints of the safety rules. In one embodiment, the safety rules are heuristic rules.

The user interface device 610 represents an embodiment of the user interface device 310 and allows the user (including a patient or clinician) to provide input relevant to therapy objectives, such as to switch programs or change operational use of the programs. The user interface device 610 includes a display screen 612, a user input device 614, and may implement or couple to the parameter selection circuit 622, or data provided from the data analysis computing system 650. The display screen 612 may include any type of interactive or non-interactive screens, and the user input device 614 may include any type of user input devices that supports the various functions discussed in this document, such as a touchscreen, keyboard, keypad, touchpad, trackball, joystick, and mouse. The user interface device 610 may also allow the user to perform other functions where user interface input is suitable (e.g., to select, modify, enable, disable, activate, schedule, or otherwise define a program, sets of programs, provide feedback or input values, or perform other monitoring and programming tasks). Although not shown, the user interface device 610 may also generate a visualization of such characteristics of device implementation or programming, and receive and implement commands to implement or revert the program and the neurostimulator operational values (including a status of implementation for such operational values). These commands and visualization may be performed in a review and guidance mode, status mode, or in a real-time programming mode.

The controller 630 can be a microprocessor that communicates with the external telemetry circuit 640, the external communication device 618, the external storage device 616, the programming control circuit 620, the parameter selection circuit, and the user interface device 610, via a bidirectional data bus. The controller 630 can be implemented by other types of logic circuitry (e.g., discrete components or programmable logic arrays) using a state machine type of design. As used in this disclosure, the term "circuitry" should be taken to refer to discrete logic circuitry, firmware, or to the programming of a microprocessor.

The data analysis computing system 650 is configured to operate treatment action circuitry 660, which may produce or initiate certain actions on the basis of device data (received and processed by device data processing circuit 652) and freeform input text (received and processed by text processing circuit 654). The treatment action circuitry 660 may identify one or more actions related to the neurostimulation treatment, and provide outputs to a patient or a clinician using patient output circuitry 662 or clinician output circuitry 664 respectively. Such outputs and actions provided by the outputs are based on the evaluation and detection of particular patient states and device states from freeform text and associated device data, discussed in more detail below.

The data analysis computing system 650 also is depicted as including a storage device 656 to store or persist data related to the device data, freeform text input, patient or clinician output, and related settings, logic, or algorithms. Other hardware features of the data analysis computing system 650 are not depicted for simplicity, but are suggested from functional capabilities and operations in the following figures.

As will be understood, patients who are experiencing chronic pain are often willing to provide detailed information regarding their current medical state within freeform text answers to questions. Freeform text in the form of a narrative, explanatory statement, or interjection is easy for patients to produce, and can provide many details regarding a patient's actions, physiological and physiological state, prior historical events, and can reflect both objective and subjective results of neurostimulation treatment. Freeform text, however, can be time-consuming or difficult for physicians and clinicians to interpret, especially when patient feedback may be contradictory (e.g., "I felt good in the morning but was unable to do any activity") or is incomplete without additional context (e.g., "I was unable to get out of bed."). Capturing patient feedback with the present systems may provide many new data points for treatment outcomes, and provide a basis for determining whether or why a particular neurostimulation treatment (and treatment program, programming value, programming effect) is or is not effective.

Prior approaches for obtaining feedback from neurostimulation have often attempted to collect subjective data from a patient regarding specific aspects of pain or treatment. Often, prior approaches would use constrained inputs such as visual or numerical scales of pain or discomfort, multiple choice questions and answers, or structured inputs to obtain information from a patient. These inputs often fail to capture the nuance and the significance of historical events, and do not capture the surrounding context that is occurring from a patient. In contrast, the following approaches provide a system which can efficiently and quickly interpret patient text, determine a patient state based on the interpreted patient text, and produce useful outcomes for diagnosis, treatment, and remediation relevant to neurostimulation device operation.

Figure 7:
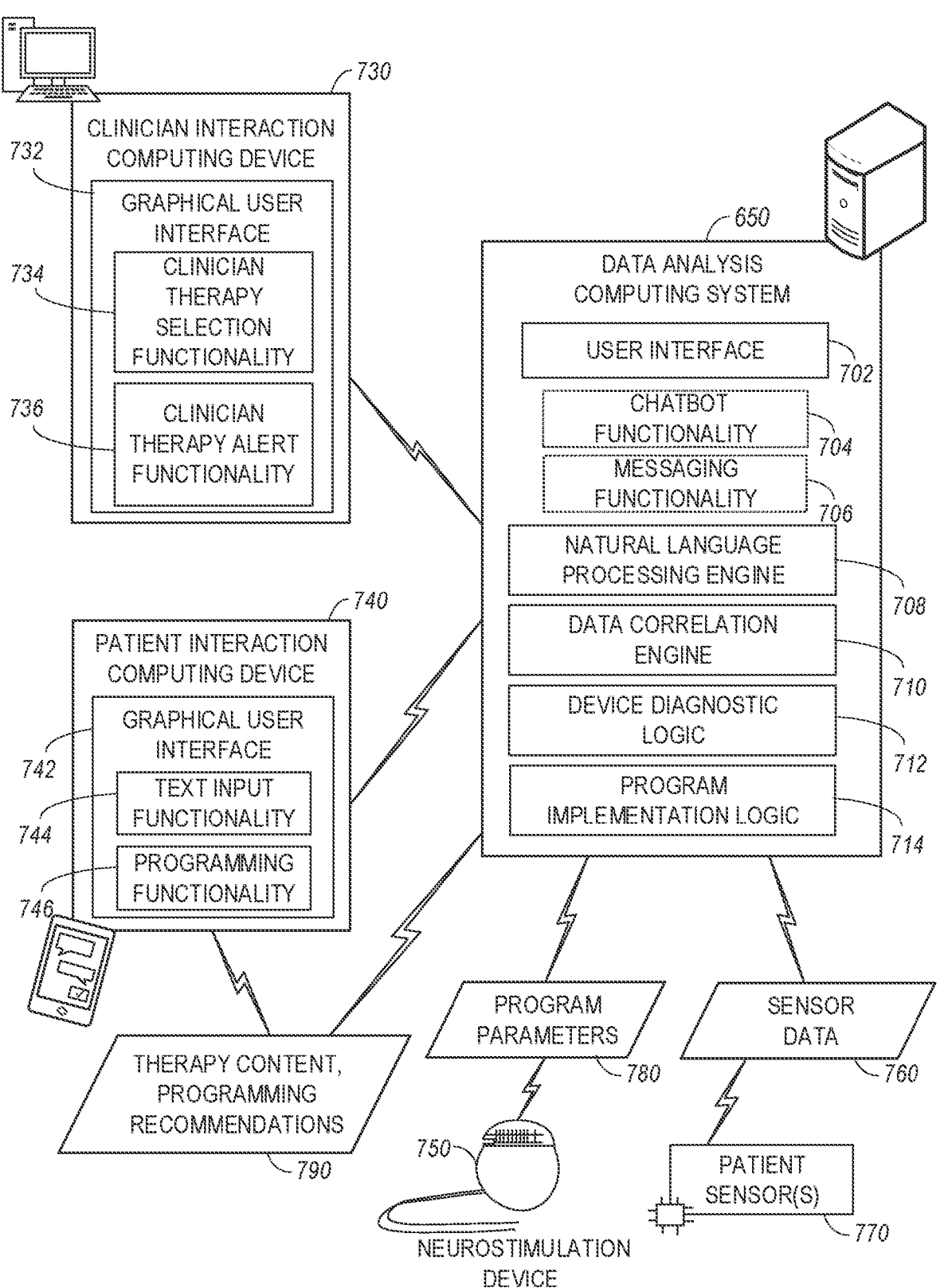
FIG. 7 illustrates, by way of example, an embodiment of data interactions among a data analysis computing system and clinician and patient interaction computing devices, for operation or monitoring of a neurostimulation device based on text input analysis.

FIG. 7 illustrates, by way of example, an embodiment of data interactions among the data analysis computing system 650 and clinician and patient interaction computing devices 730, 740, for operation of a neurostimulation device 750 based on freeform text input analysis. At a high level, the data analysis computing system 650 identifies operations related to the neurostimulation treatment based on the analysis of input text, such as diagnostic actions, alerts, content or programming recommendations, or programming actions. Such programming actions (and, operational actions based on programming recommendations) may be implemented on the neurostimulation device 750 (e.g., using the programming techniques discussed above). The data analysis computing system 650 identifies and initiates these actions through the execution of one or more data analysis engines, such as a natural language processing engine 708 which parses and determines a state of a human patient from freeform text input, and data correlation engine 710 which determines a state of treatment from historical or current operation of the neurostimulation device 750. In some examples, the determined state of treatment may be based on correlating the historical use of a neurostimulation program or set of parameters with the current state of a patient (e.g., identifying that a pain condition became worse after beginning use of a particular program at a previous point in time).

Specifically, the data analysis computing system 650 operates natural language processing engine 708 to analyze text input originating from a human patient that is relevant to neurostimulation treatment. The analysis of text input may occur using one or more forms of text parsing, linguistic analysis, The text input may be received via a user interface 702 of the data analysis computing system 650, such as provided from chatbot functionality 704 or messaging functionality 706. The text input also may be provided from a patient interaction computing device 740, or other third party devices and platforms not depicted. Additional detail of the chatbot functionality 704 and the messaging functionality 706 is discussed with reference to the user interfaces of FIGS. 8A and 8B, below.

The data analysis computing system 650 also operates data correlation engine 710 to correlate (e.g., identify, match, associate) device state data and patient state data, device diagnostic logic 712 to evaluate operational or conditions from the neurostimulation device 750, and program implementation logic 714 to effect changes in programming to the neurostimulation device 750. In an example, the program implementation logic 714 enables control, modification, selection, or specification of neurostimulation programming parameters, in an automatic, suggested, or manual fashion. Additional detail regarding programming of the device 750 is provided with reference to FIG. 10, and it will be understood that other embodiments of program modeling, selection, recommendation, and implementation may be provided via programming devices, data services, or information services which are not depicted.

In an example, the natural language processing engine 708 applies one or more approaches for analysis of text. One such approach may include topic modeling, which is an unsupervised machine learning approach that can be used to discover and identify topical concepts from a corpus of text. For example, a natural language processing model which uses topic modeling may be trained on related text topics, and then deployed to identify if a text comment is on-topic to the use of a neurostimulation or not (e.g., to determine relevancy of the text to one or more topics). Topic modeling may also be used to identify different troubleshooting areas relevant to operation of a neurostimulation device such as charging, remote controls, etc.

In an example, the patient interaction computing device 740 is a computing device (e.g., personal computer, tablet, smartphone) or other form of user-interactive device which receives and provides interaction with a patient using a graphical user interface 742, text input functionality 744, and programming functionality 746. For instance, the text input functionality 744 may receive freeform text from a patient via questionnaires, surveys, messages, or other textual inputs. Such inputs may provide text related to pain or satisfaction, that can be used to identify a psychological or physiological state of the patient, neurostimulation treatment results, or related conditions. Although not depicted, other forms of non-text input functionality may also be provided.

The patient interaction computing device 740 is also depicted as including the programming functionality 746, to provide one or more outputs in the graphical user interface related to programming control or implementation. The programming functionality 746 specifically may provide the patient with therapy content and programming recommendations 790 generated by the data analysis computing system 650. Other form factors and interfaces such as audio interfaces and text interfaces may also be substituted for or augmented with the graphical user interface 742.

The clinician interaction computing device 730 may include a graphical user interface 732, which implements clinician therapy selection functionality 734 and clinician therapy alert functionality 736, offering similar capabilities to the graphical user interface 742 for the patient, but adapted for use by a clinician (e.g., to provide enhanced functionality or features for physician control). Although not depicted, the therapy content and programming recommendations 790 and enhanced information provided for clinicians can also be presented via the graphical user interface 732.

In an example, the data analysis computing system 650 generates, selects, or communicates therapy content and programming recommendations 790 to the patient interaction computing device 740 or clinician interaction computing device 730. Such content and recommendations 790 are provided based on aspects of a correlated patient and device state, from a patient state detected from free text processing. The therapy content and programming recommendations 790 may include a recommendation or identification of the type of therapies to apply, instructions, recommendations, or feedback (including clinician recommendations, behavioral modifications, etc., selected for the patient). The therapy content and recommendations 790 also may provide relevant information based on the sensor data 760 or other neurostimulation state monitoring performed on the patient.

The data analysis computing system 650 may utilize sensor data 760 from one or more patient sensors 770 (e.g., wearables, sleep trackers, motion tracker, implantable devices, etc.) among one or more internal or external devices. The sensor data 760 may be used in addition to the program parameters 780, to determine a customized and current state of the patient condition or neurostimulation treatment results. In various examples, the neurostimulation device 750 includes sensors which contribute to the sensor data 760 evaluated by the data analysis computing system 650.

In an example, the patient sensors 770 are physiological or biopsychosocial sensors that collect data relevant to physical, biopsychosocial (e.g., stress and/or mood biomarkers), or physiological factors relevant to a state of the patient Examples of such sensors might include a sleep sensor to sense the patient's sleep state (e.g., for detecting lack of sleep), a respiration sensor to measure patient breathing rate or capacity, a movement sensor to identify an amount or type of movement, a heart rate sensor to sense the patient's heart rate, a blood pressure sensor to sense the patient's blood pressure, an electrodermal activity (EDA) sensor to sense the patient's EDA (e.g., galvanic skin response), a facial recognition sensor to sense the patient's facial expression, a voice sensor (e.g., microphone) to sense the patient's voice, and/or an electrochemical sensor to sense stress biomarkers from the patient's body fluids (e.g., enzymes and/or ions, such as lactate or cortisol from saliva or sweat). Other types or form factors of sensor devices may also be utilized.

The following examples focus on various types of user interfaces and interactions which directly receive textual input from a human patient. It will be understood that the text processing performed by the present approaches may occur on a variety of text input and sources of text content Such text content may include the results from voice-to-text converted from voice phone or online calls with a medical device representative or a patient care entity. Further, it will be understood that relevant text data may be provided from voice, text, or multi-modal input from multiple channels (e.g., SMS text messages, an email, an app, a website, a chatbot, a virtual universe meeting, etc.). Moreover, such text data may be provided from the conversion of voice-to-text from in-app voice recordings, voice chats, voicemails, or voice interactions with virtual assistants or agents (e.g., Amazon® Alexa, Google® Assistant, Apple® Siri, etc.). Analysis may also be performed on voice recordings directly to obtain relevant characteristics, such as to identify the vocal tone of the statement (e.g., analyzing the auditory signal itself to identify physiological or psychological characteristics of the human patient such as calmness, irritation, sadness, etc.).

Figures 8A, 8B:
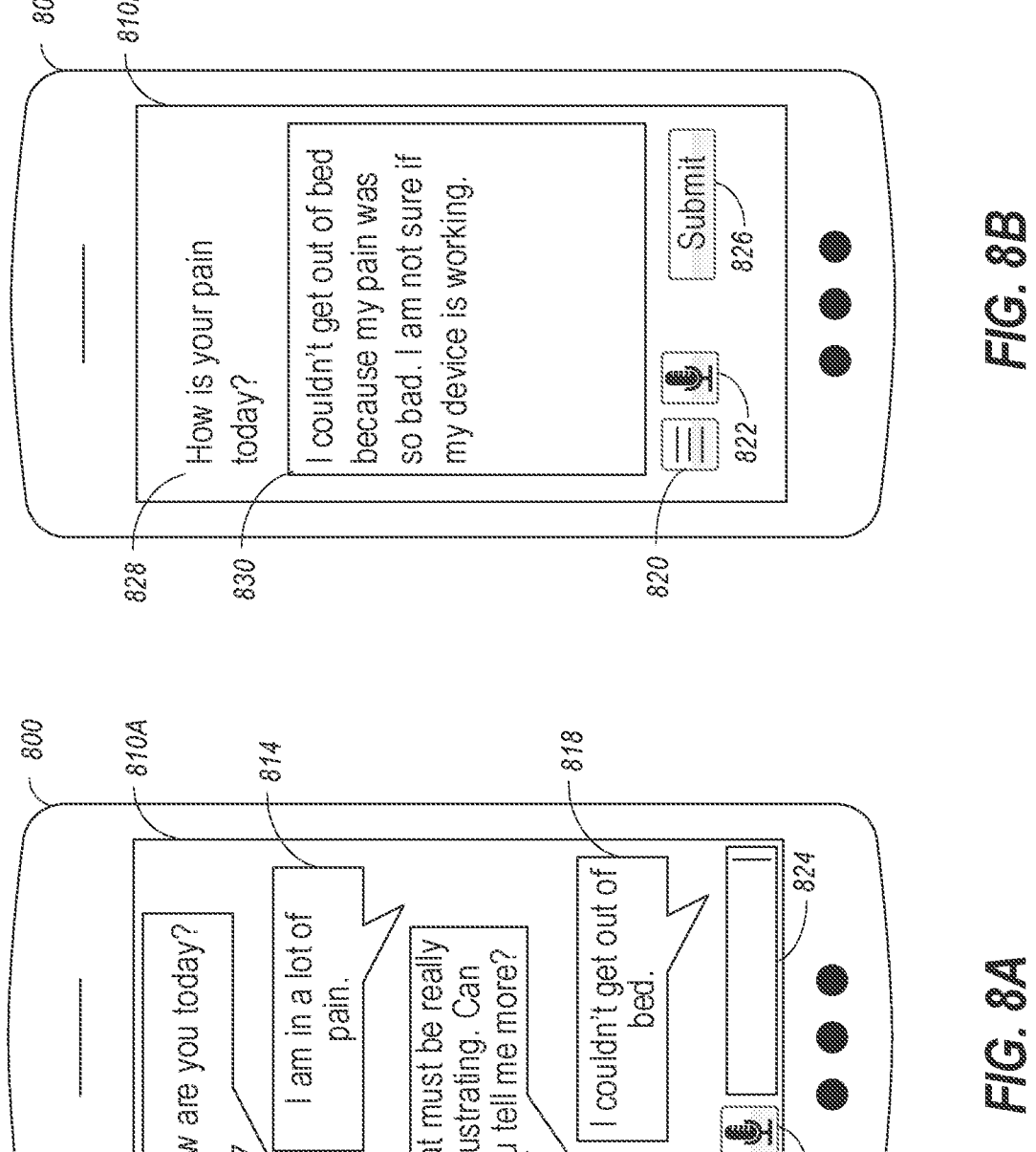
FIGS. 8A and 8B illustrate, by way of example, embodiments of varied user interfaces for receiving textual input from a human patient.

FIGS. 8A and 8B illustrate, by way of example, variations of user interfaces for receiving textual input from a human patient. Specifically, the user interface 810A provided in FIG. 8A demonstrates the use of a graphical user interface to collect freeform text replies, provided in an automated chatbot session. Likewise, the user interface 810B provided in FIG. 8B demonstrates the use of a graphical user interface to collect freeform text, in the form of a narrative or answer to a question. It will be understood that the user interfaces 810A, 810B provide high level illustrations, and do not fully depict many features of a user interface.

In additional detail, the user interface 810A is depicted as operating on a mobile computing device 800, includes a series of questions and responses 812, 816, accompanied with patient responses 814, 818. The sequential nature of the questions and responses 812, 816 encourages the patient to provide specific, focused responses about their physiological condition and the effectiveness of neurostimulation treatment. The user interface 810A also includes user interface functionality such as in the form of a keyboard control 820, a speech recognition control 822, and an input text box 824. The series of questions and responses which are provided to the patient may be implemented by a chatbot, a script or dialogue, a human actor, or other automated or manual entities.

In contrast, the user interface 810B is depicted as also operating on the mobile computing device 800, including controls 820, 822, and a submission control 826. Here, the user interface 810B also presents one or more free text questions 828 which are offered as part of a patient questionnaire. Here, the illustrated question is "How is your pain today?", providing an open-ended invitation for freeform text user input from a text interaction 830 in a text input field. The text interaction 830 illustrates the result of user input, with example text provided by a patient: "I couldn't get out of bed because my pain was so bad. I am not sure if my device is working." The open-ended nature of the question 828, and the freeform nature of the text interaction 830 is used to elicit detail that might not otherwise arise from scripted or pre-populated questions.

The information that is obtained from the patient in the interactions of user interfaces 810A, 810B may be collected and analyzed from multiple interactions to detect persistent conditions, new conditions, or trends. For instance, a patient may interact with the questionnaire or the chatbot over period of days, weeks, and months, to observe changes and identify additional detail as more text is provided by the patient. Each text interaction may be processed to determine a particular state of a patient at a particular time, which is then scored, recorded, and compared over time to other interactions.

In further examples, an algorithm provided by a natural language processing engine translates the captured interactions to polarity (valence) scores. These polarity scores, which are paired with timestamps, then can be cross-referenced against device data (e.g., program usage, device on/off state, physiological state from a sensor, etc.). As discussed below, the polarity of a particular text statement may be directly determined as a result of sentiment analysis performed using any number of natural language processing techniques. The polarity of a text statement and the resulting patient state may be used, for instance, to identify the most effective settings of a neurostimulation program, directly from patient feedback and responses collected over time. In a further example, individual polarity scores may not necessarily be robust or fully indicative of a patient state. As a result, one or more filters may be applied to polarity values over time (including, in the simplest form, a moving average), so that polarity is not improperly sensitive to individual comments. Additionally, it will be understood that some neurostimulation programming settings may have a longer effect or relevance (e.g., the text comments provided by a patient may be relevant to the program used a number of hours ago, and not the current program). A filtering mechanism may be used to take such changes and time-based effects into account.

Figure 9A:
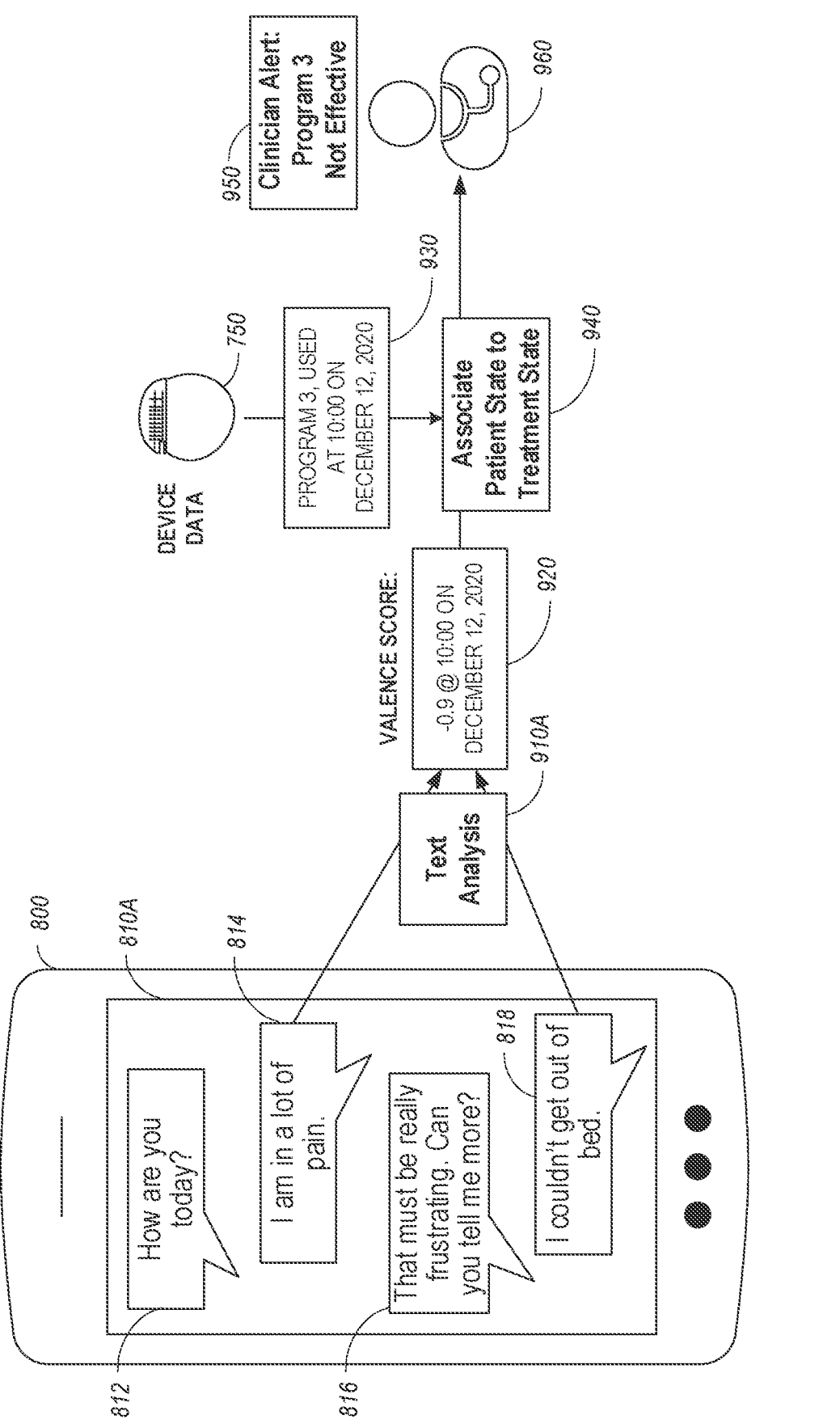
FIGS. 9A, 9B, and 9C illustrate, by way of example, embodiments of data processing operations being performed on freeform text entered by a human patient into respective user interfaces.
Figure 9B:
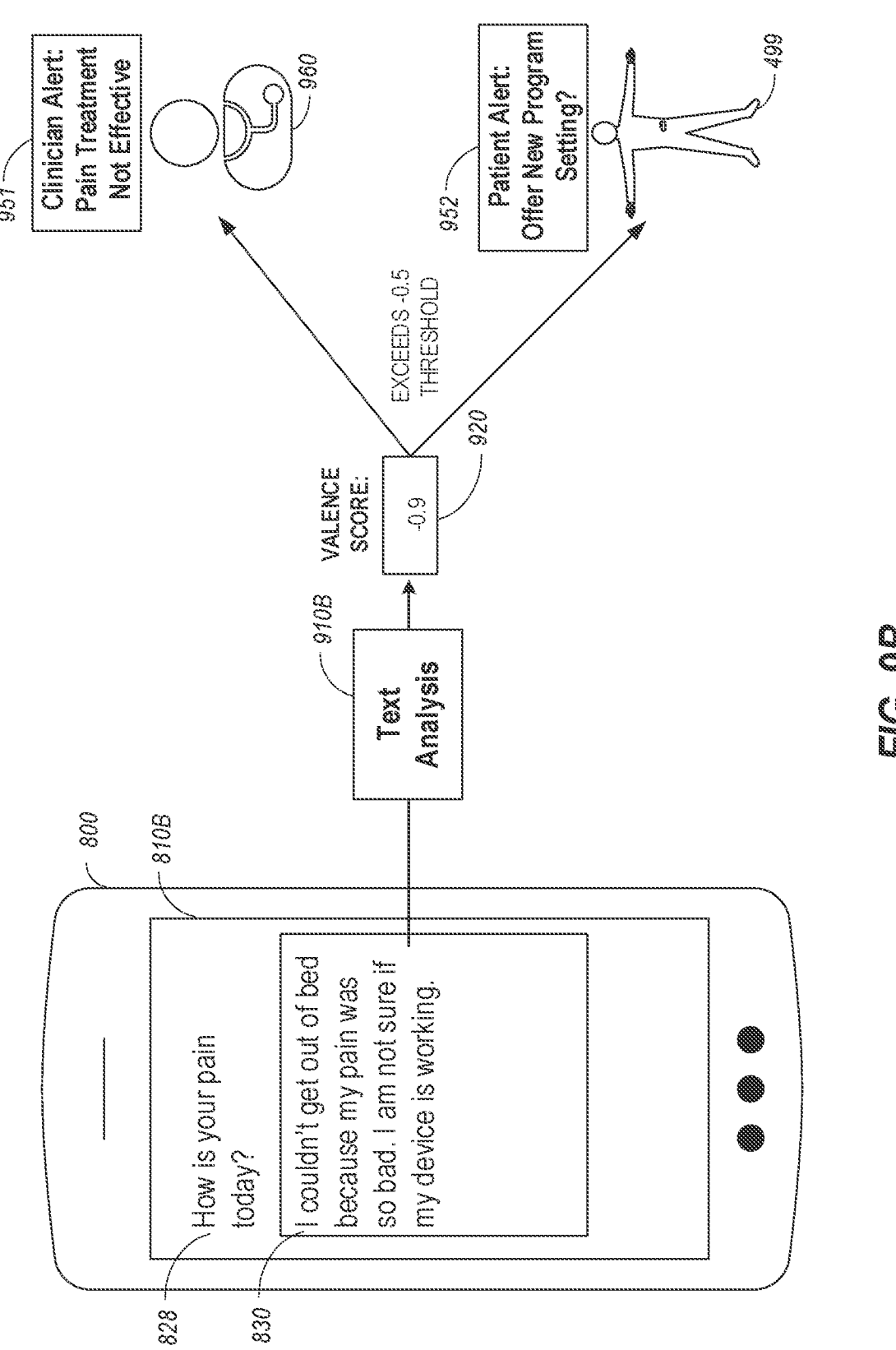
Figure 9C:
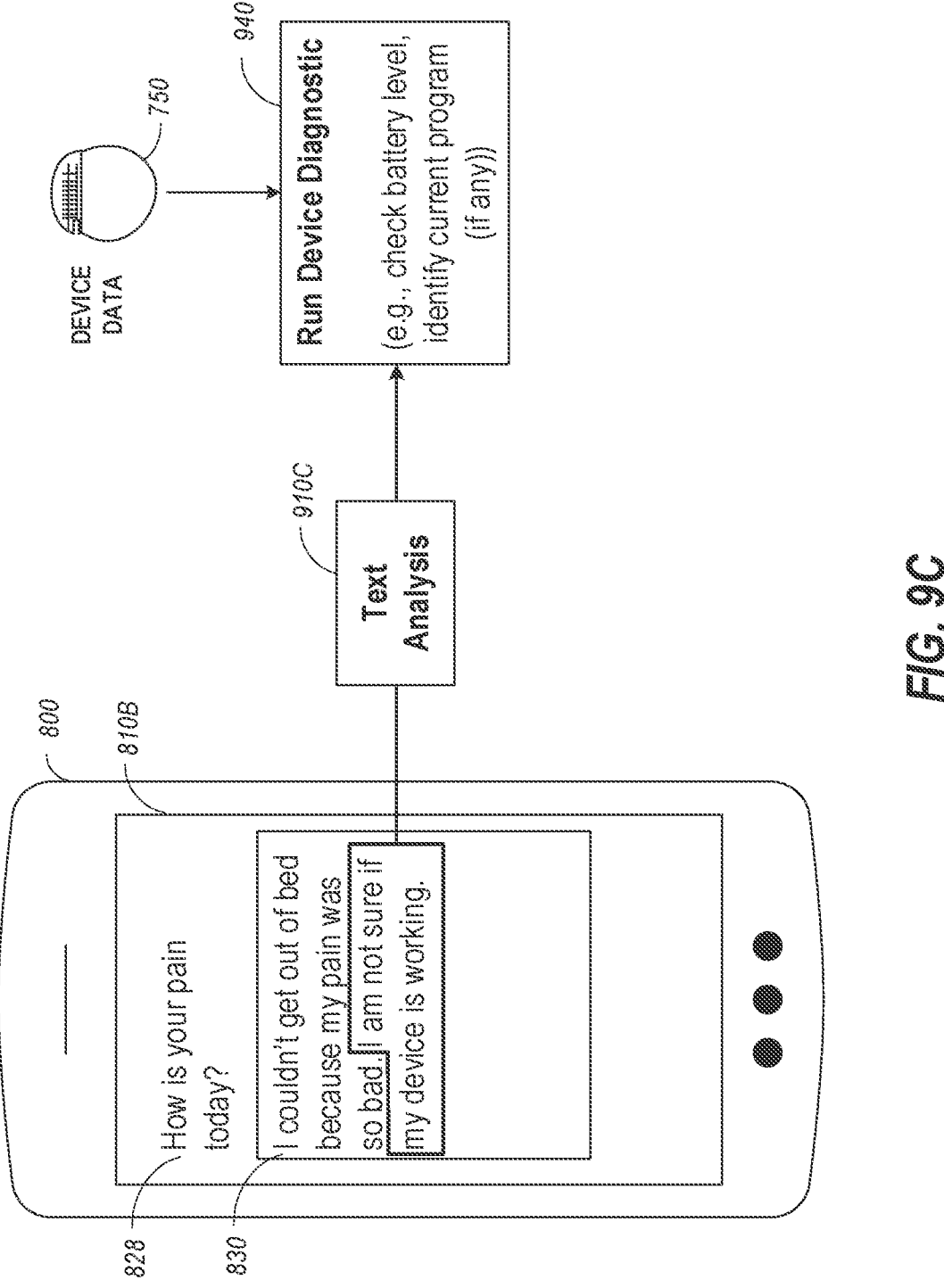

FIGS. 9A, 9B, and 9C illustrate, by way of example, data processing operations being performed on text entered into the user interfaces 810A, 810B. In the example of FIG. 9A, the text interactions 814, 818 provided from the patient are evaluated with text analysis operations 910A, to produce a valence score 920. For instance, the valence score 920 may represent a negative or positive sentiment (e.g., in a range from values −1 to +1) captured at or associated with a particular time. The valence score 920 or its derivative may also represent other attributes such as intensity (e.g., the amount of positive or negative sentiment), or be provided as a weighted or composite score.

The valence score 920 provides a data point for a particular patient state at a point in time, which can be associated with a device state at the same point in time. This device state may originate from device data 930 provided from the neurostimulation device 750. Based on a matching or other correlation of the valence score 920 to the device data 930, a patient state (represented by the valence score) can be associated 940 to a treatment state. This associated patient and treatment state may be used to trigger an action, such as a clinician alert 950 to a clinician 960 (e.g., device manufacturer representative, doctor, etc.), relating to a neurostimulation program (e.g., indicating that the program used at the point in time is not effective).

In the example of FIG. 9B, similar operations are performed to determine and initiate relevant actions. Here, the text interaction 830, originating from the patient, is evaluated with text analysis operations 910B. Although multiple statements are provided in the text interaction 830, a single valence score 920 is produced, representing a composite score for the multiple statements. The valence score 920 is compared with a threshold, such as the –0.5 negative threshold as depicted. Because the valence score –0.9 exceeds this negative threshold, action is taken. Here, the action includes a first action providing a clinician alert 951 that the pain treatment is not effective, and a second action providing a patient alert 952 with an option to implement a new program setting.

a detection algorithm may be used to identify complaints regarding the device, program, or treatment plan. Consider the text written by a patient, "Too many details to write here. I would like to talk to my doctor." Although this text does not directly indicate a problem or what the problem is, the patient is providing a complaint regarding the outcome of treatment and the need for clinical intervention. Similar aspects of triage, device diagnostics, remediation, or logging may be used based on the detection of such complaints.

In a specific example, a natural language processing algorithm may be implemented with use of a rule-based sentiment analyzer. One such example of a sentiment analyzer is the VADER (Valence Aware Dictionary for sEntiment Reasoning) model, which uses a list of lexical features (e.g., words) that are positive or negative. This model is sensitive to both polarity (positive/negative) and intensity (strength) of emotion indicated within text. It will be understood that other models may be trained or turned with specific consideration of pain treatment and physiological conditions, and analysis or data values from multiple models may also be considered. Further, it will be understood that words can be masked or de-emphasized as part of the analysis. For instance, commonly used words such as "pain" may not be helpful for assessing user sentiment, and may require consideration of surrounding words or phrases.

TABLE 1

| Pain Statements | | | | |
| --- | --- | --- | --- | --- |
| Pain Statement | Negative | Neutral | Positive | Compound |
| "I swept the floor! Without any pain" | 0 | 0.625 | 0.375 | 0.4577 |
| "Can not tolerate any program that I can feel. It increases my pain dramatically." | 0.216 | 0.784 | 0 | –0.5106 |
| "No comment" | 0 | 1 | 0 | 0 |

TABLE 2

| Sleep Statements | | | | |
| --- | --- | --- | --- | --- |
| Sleep Statement | Negative | Neutral | Positive | Compound |
| "Feeling lot better" | 0 | 0.185 | 0.815 | 0.5267 |
| "The procedure area was causing increased pain. I got very little sleep due to this." | 0.190 | 0.690 | 0.121 | –0.2960 |
| "Staying about the same." | 0 | 1 | 0 | 0 |

In the example of FIG. 9C, the text interaction 830 provided from the patient is evaluated with text analysis operations 910C, to identify individual statements. Such text analysis operations may use keyword matching, such as related to device keywords "device", "working" and like semantic concepts. Such text analysis operations may also use topic modeling, to determine whether a particular text statement is or is not relevant to particular neurostimulation device features or device operations. Based on the text analysis 910C, an action is identified to initiate device diagnostics 940. The use of the device diagnostics 940 may evaluate various aspects of device data from the neurostimulation device 750. This may include, checking current battery level, identifying a current program, identifying device impedance, verifying program settings, performing logging or evaluation of logging information, initiating troubleshooting procedures, and the like.

Other forms of natural language processing or rules may be used to identify or trigger specific actions. For instance, A triage that is performed from text analysis sentiment values can help make it easier for clinicians (including device manufacturer representatives, physicians, etc.) to identify which patients are in need of what technical support. The text analysis sentiment values can also help identify the types and variations of therapies that are effectively meeting patients' treatment needs. It will be understood that the collection text may extend into a variety of settings, being integrated into multiple products/apps, including feedback captured during patients' normal activities, clinician visits, and other events, thus capturing a more realistic view of a patient state.

Figure 10:
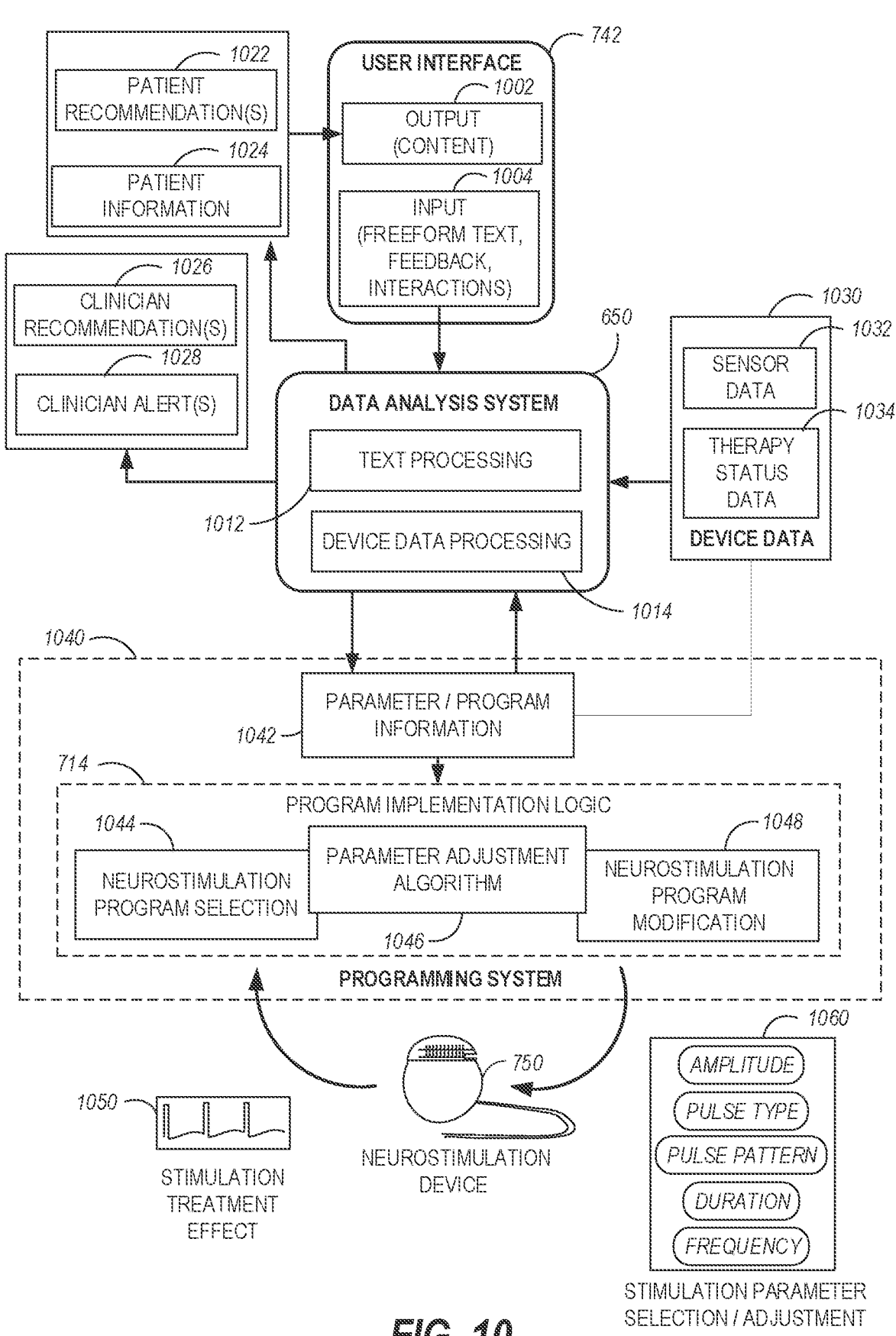
FIG. 10 illustrates, by way of example, an embodiment of a data processing flow for affecting the neurostimulation treatment of a human patient, based on text and device data processing.

FIG. 10 illustrates, by way of example, an embodiment of a data processing flow affecting the neurostimulation treatment of a human patient, based on implemented text processing 1012 and device data processing 1014 functions. Here, additional details are provided on the data flow between the data analysis computing system 650, an example user interface (graphical user interface 742). Other user interfaces and actions are not depicted for simplicity.

In this example, input 1004 (e.g., freeform text, patient feedback, interaction results) is obtained by the data analysis computing system 650 from user interface 742. FIG. 10 also depicts the evaluation of device data 1030, such as sensor data 1032, therapy status data 1034, and other treatment aspects which may be obtained or derived from the neurostimulation device or related neurostimulation programming. Also in this example, output 1002 (e.g., content) is obtained from the data analysis computing system 650 at user interface 742, such as in the form of patient recommendations 1022, or patient information 1024. The data analysis computing system 650 may separately provide clinician recommendations 1026, clinician alerts 1028, or other related actions.

The remainder of the data processing flow illustrates how data processing results from the data analysis computing system 650 can be used to effect programming, such as in a closed loop (or partially-closed-loop) system. A programming system 1040 uses parameter or program information 1042 provided from the data analysis computing system 650 as an input to program implementation logic 714. The program implementation logic 714 may be implemented by a parameter adjustment algorithm 1046, which affects a neurostimulation program selection 1044 or a neurostimulation program modification 1048. For instance, some parameter changes may be implemented by a simple modification to a program operation; other parameter changes may require a new program to be deployed. The results of the parameter or program changes or selection results in definition or adjustment to various stimulation parameters 1060 at the neurostimulation device 750, causing a different or new stimulation treatment effect 1050.

By way of example, operational parameters of the neurostimulation device which are generated, identified, or evaluated by the present systems and techniques may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The neurostimulator may use current or voltage sources to provide the neurostimulator output, and apply any number of control techniques to modify the electrical simulation applied to anatomical sites or systems related to pain or analgesic effect. In various embodiments, a neurostimulator program may be defined or updated to indicate parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use.

FIGS. 11A and 11B illustrate, by way of example, detailed sequences 1100, 1120 of how textual input may be evaluated by a natural language processing engine, and used to initiate specific actions. Although sequences 1100, 1120 are depicted as separate sequences, it will be understood that the sequences may be combined or integrated with either other (or, into the processing method 1200 of FIG. 12, discussed below).

The sequence 1100 details a process of text sentiment evaluation, beginning with operations to obtain and process textual input with a natural language processing engine (operation 1102) and identifying sentiment of the respective text statements of the textual input (operation 1104). Such sentiment may be expressed by a combination of negative, neutral, and positive sentiment values. The sentiment values for each statement are used to calculate a composite sentiment value applicable to multiple statements (operation 1106), based on the negative, neutral, and positive values for each statement. Examples of negative, neutral, and positive sentiment analysis is discussed above with reference to Tables 1 and 2.

The sentiment evaluation continues with the comparison of the composite sentiment values to one or more threshold values (operation 1108). One or more actions may be initiated based on the composite sentiment (operation 1110).

The sequence 1120 details a similar process of text evaluation, from a perspective of the state of the device and the patient, which is evaluated and used to initiate particular activities. The sequence begins with operations to obtain and process the textual input with a natural language processing engine (operation 1122) and obtain and process device data from a neurostimulation device (operation 1124). Here, the state of the patient, indicated by the textual input (e.g., using sentiment analysis in operations 1104-1106), is matched to a particular state of the neurostimulation device (operation 1126), indicated by device data. Such matching may establish an association between a particular patient state and a particular device state at an identified time or time range. Based on the time or time range of the data, the particular patient state may indicate a historical state (e.g., occurring at a previous time or times), an aggregated or composite state (e.g., an average or combination of states over a period of time or times), or a current state (e.g., current to the time of measurement and evaluation).

The actions that are initiated based on the matched patient and device state may include one or more of: providing an alert to a clinician (operation 1128); providing activity, behavior, and therapy recommendations to the patient (operation 1130); providing a change (or, offering a recommended change) to the neurostimulation program or a neurostimulation programming setting (operation 1132); or, performing a diagnostic action of the neurostimulation device (operation 1134).

FIG. 12 illustrates, by way of example, an embodiment of a processing method 1200 implemented by a system or device for use to evaluate a neurostimulation treatment provided from a neurostimulation device (e.g., an implantable electrical neurostimulation device), based on evaluated text content. For example, the processing method 1200 can be embodied by electronic operations performed by one or more computing systems or devices that are specially programmed to implement the data analysis and/or neurostimulation functions described herein. In specific examples, the operations of the method 1200 may be implemented through the systems and data flows depicted above in FIGS. 6 to 11B.

In an example, the method 1200 begins by obtaining text content (operation 1202), such as is discussed above with reference to the textual analysis discussed among FIGS. 8A to 9C. Such text content may indicate or relate to the state or the condition of a human patient, such as with text content originating from conversations or feedback received from the human patient. In specific examples, the text content originates from at least one of: text provided in a text chat session (e.g., transcript text) conducted between a chatbot and the human patient; a voice chat session conducted between a virtual agent and the human patient, with at least a portion of the voice chat session converted to text (e.g., a transcript of the chat session conversation); a text message session conducted between a text service and the human patient (e.g., a transcript of one or more SMS text conversations); or an audio recording of a discussion conducted between the human patient and a human agent, with at least a portion of the audio recording converted to text (e.g., a transcript of the audio recording); or a freeform text input provided by the human patient (e.g., survey or question responses, narrations, etc.).

The method 1200 continues by identifying a state of the human patient (e.g., a historical, current, or composite state of the patient), from natural language processing of the text content (operation 1204). The inputs may be analyzed according to the approaches discussed with FIGS. 11A and 11B, indicated above, including variations of sentiment analysis, topic modeling, among other techniques. In an example, the state of the human patient includes or is associated with one or more physiological condition identified using the natural language processing. Such a physiological condition may relate to one or more of: pain, sleep, movement, medication, or emotional state, for the human patient.

In specific examples, operations to identify the state of the human patient include use of sentiment analysis, such as with processing operations that identify a sentiment of at least one statement provided in the text content, using a trained natural language processing model. Using the sentiment of the at least one statement, the state of the human patient may be determined (e.g., predicted or classified). In a further example, the sentiment of the at least one statement includes a calculated sentiment value that is compared with a threshold sentiment value. For instance, the calculated sentiment value may be produced from a negative sentiment value, a neutral sentiment value, and a positive sentiment value that is calculated for each of the at least one statement. In a further example, whether or not an action for the neurostimulation treatment is initiated (e.g., at operation 1212, discussed below), is determined based on the calculated sentiment value exceeding some threshold sentiment value. Other actions or states may also be dependent on the results of the sentiment analysis or other natural language processing determinations or classifications.

The method 1200 continues by obtaining device data related to a neurostimulation treatment (operation 1206). Such device data may be obtained directly or indirectly from the neurostimulation device, or data associated with the neurostimulation device, relating to an implantable neurostimulation device being used for neurostimulation treatment of the human patient. The method 1200 continues by identifying a state of the neurostimulation treatment from the device data (operation 1208). In an example, the state of the neurostimulation treatment comprises at least one device condition identified from the device data. Such a device condition may relate to one or more of: power status, program usage, battery level, impedance, device settings, or scheduled cycles, for the neurostimulation device.

The method 1200 continues to associate the identified state of the patient with the identified state of neurostimulation treatment (operation 1210). In an example, the operations to associate the identified state of the human patient to the identified state of the neurostimulation treatment may be performed may be performed by evaluating historical or current use of the neurostimulation program. For example, such use may be determined by matching use of at least one neurostimulation program to the identified state of the human patient. In a specific example, use of the at least one neurostimulation program may be identified based on a time of the use of the at least one neurostimulation program, matched to at least one time associated with the identified state of the human patient. Based on this associated state, an action may be identified and this identified action may be initiated for use with the human patient, as detailed in the following operation.

The method 1200 concludes with operations to initiate an action for the neurostimulation treatment based on one or more identified states of the patient and the associated neurostimulation treatment (operation 1212). In one example, the initiated action may include providing (or causing) an alert to a clinician or a customer assistance entity associated with the neurostimulation treatment of the human patient. Such an alert may provide information for the identified state of the human patient and the identified state of the neurostimulation treatment. In another example, the initiated action may perform (or cause) a diagnostic action on the neurostimulation device. In yet another example, the initiated action includes providing (or causing) activity, behavior, or therapy recommendations to the human patient. In yet another example, the initiated action comprises changing or offering a change (or, causing such a change) to a neurostimulation programming setting on the neurostimulation device, for a neurostimulation programming setting that is associated with the neurostimulation treatment of the human patient. Multiple of such actions may be initiated and used.

Consistent with the neurostimulation device programming approaches described with reference to FIGS. 1 to 6 above, an initiated action that provides a change to the neurostimulation programming setting may effect a change in operation of a programmed neurostimulation device. The initiated action may include identifying programming values for at least one neurostimulation programming parameter in a neurostimulation program, based on the identified state of the human patient that is associated to the identified state of the neurostimulation treatment. The resulting identified programming values may specify a change in operation of the neurostimulation program for one or more of: pulse patterns, pulse shapes, a spatial location of pulses, waveform shapes, or a spatial location of waveform shapes, for modulated energy provided with a plurality of leads of the neurostimulation device.

Although many of the preceding examples were provided with reference to spinal cord stimulation for introducing pain analgesia, it will be understood that the present techniques for freeform text and device data analysis may also be applicable to other forms of neurostimulation. For instance, a variation for deep brain stimulation may be specifically tailored to identify free text feedback relating to motor symptoms or patient motor capabilities.

FIG. 13 illustrates, by way of example, a block diagram of an embodiment of a system 1300 (e.g., a computing system) implementing freeform text or related device data analysis to monitor, modify, or effect operation and output of a neurostimulation programming mode. The system 1300 may be integrated with or to a remote control device, patient programmer device, clinician programmer device, program modeling system, or other external device, usable for the adjustment of neurostimulation programming. In some examples, the system 1300 may be a networked device connected via a network (or combination of networks) to a programming device or programming service using a communication interface 1308. The network may include local, short-range, or long-range networks, such as Bluetooth, cellular, IEEE 802.11 (Wi-Fi), or other wired or wireless networks.

The system 1300 includes a processor 1302 and a memory 1304, which can be optionally included as part of input and weighting control circuitry 1306. The processor 1302 may be any single processor or group of processors that act cooperatively. The memory 1304 may be any type of memory, including volatile or non-volatile memory. The memory 1304 may include instructions, which when executed by the processor 1302, cause the processor 1302 to implement the features of the user interface, or to enable other features of the input and weighting control circuitry 1306. Thus, electronic operations in the system 1300 may be performed by the processor 1302 or the circuitry 1306.

For example, the processor 1302 or circuitry 1306 may implement any of the features of the method 1200 (such as operations 1202-1212) to obtain and process patient text and device data, identify a state of a human patient and a state of the neurostimulation treatment, and initiate an action based on the state of a human patient and the state of the neurostimulation treatment. It will be understood that the processor 1302 or circuitry 1306 may also implement aspects of the logic and processing described above with reference to FIGS. 6-12, for use in a various forms of closed-loop and open-loop device programming or related device actions.

FIG. 14 illustrates, by way of example, a block diagram of an embodiment of a system 1400 (e.g., a computing system) implementing neurostimulation programming circuitry 1406 to cause programming of an implantable electrical neurostimulation device, for accomplishing the therapy objectives in a human subject as discussed herein. The system 1400 may be operated by a clinician, a patient, a caregiver, a medical facility, a research institution, a medical device manufacturer or distributor, and embodied in a number of different computing platforms. The system 1400 may be a remote control device, patient programmer device, program modeling system, or other external device, including a regulated device used to directly implement programming commands and modification with a neurostimulation device. In some examples, the system 1400 may be a networked device connected via a network (or combination of networks) to a computing system operating a user interface computing system using a communication interface 1408. The network may include local, short-range, or long-range networks, such as Bluetooth, cellular, IEEE 802.11 (Wi-Fi), or other wired or wireless networks.

The system 1400 includes a processor 1402 and a memory 1404, which can be optionally included as part of neurostimulation programming circuitry 1406. The processor 1402 may be any single processor or group of processors that act cooperatively. The memory 1404 may be any type of memory, including volatile or non-volatile memory. The memory 1404 may include instructions, which when executed by the processor 1402, cause the processor 1402 to implement the features of the neurostimulation programming circuitry 1406. Thus, the electronic operations in the system 1400 may be performed by the processor 1402 or the circuitry 1406.

The processor 1402 or circuitry 1406 may implement any of the features of the method 1200 (including operations 1210) to identify neurostimulation programming parameters, and implement (e.g., save, persist, activate, control) the programming parameters or relevant programs in the neurostimulation device, with use of a neurostimulation device interface 1410. The processor 1402 or circuitry 1406 may further provide data and commands to assist the processing and implementation of the programming using communication interface 1408. It will be understood that the processor 1402 or circuitry 1406 may also implement other aspects of the text processing, device data processing, or device programming functionality described above with reference to FIGS. 6-12.

Figure 15:
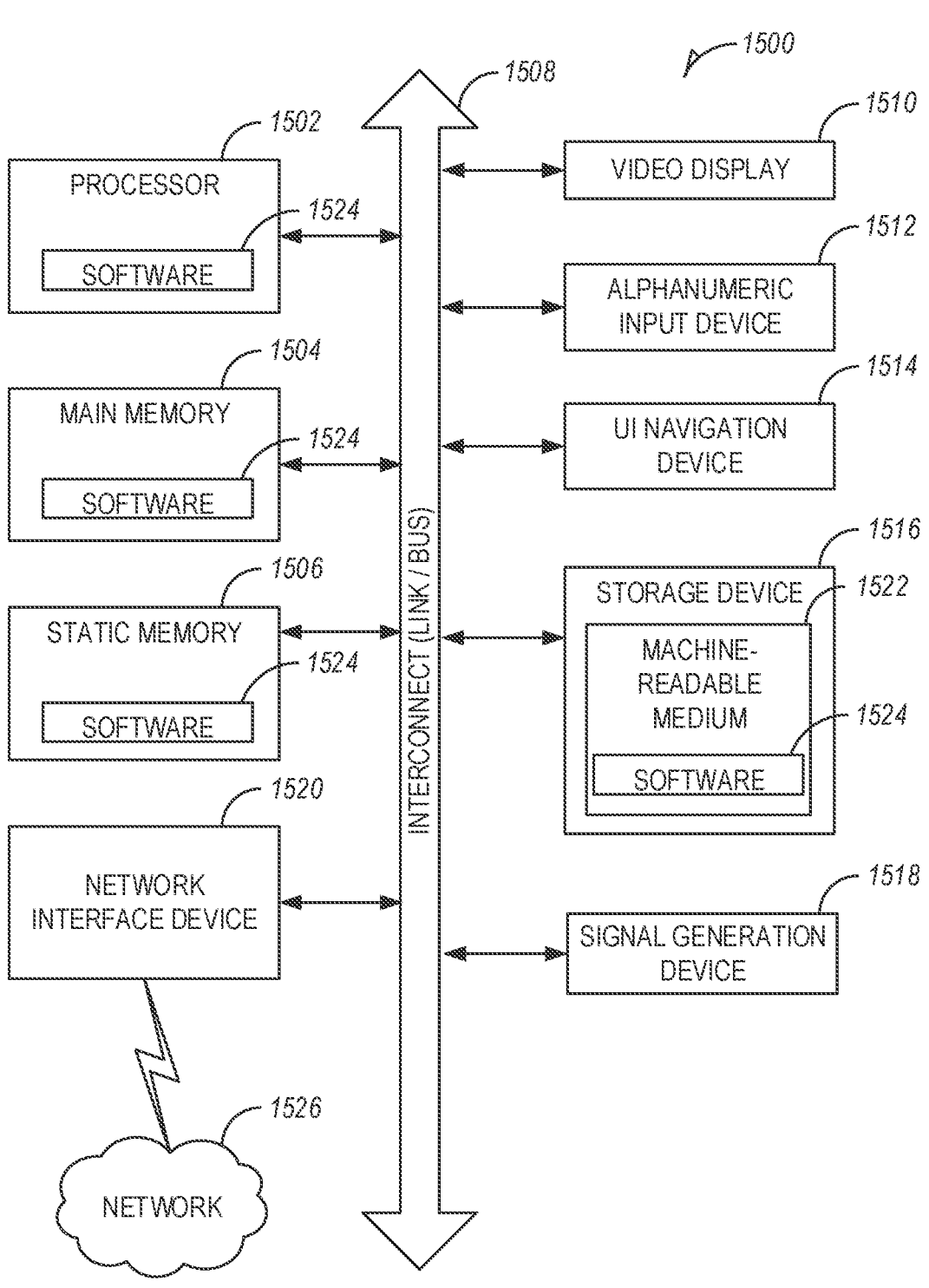
FIG. 15 is a block diagram illustrating a machine in the example form of a computer system, within which a set or sequence of instructions may be executed to cause the machine to perform any one of the methodologies discussed herein, according to an example embodiment.

FIG. 15 is a block diagram illustrating a machine in the example form of a computer system 1500, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1500 includes at least one processor 1502 (e.g., a central processing unit (CPU), a graphics processing unit (GPU) or both, processor cores, compute nodes, etc.), a main memory 1504 and a static memory 1506, which communicate with each other via a link 1508 (e.g., bus). The computer system 1500 may further include a video display unit 1510, an alphanumeric input device 1512 (e.g., a keyboard), and a user interface (UI) navigation device 1514 (e.g., a mouse). In one embodiment, the video display unit 1510, input device 1512 and UI navigation device 1514 are incorporated into a touch screen display. The computer system 1500 may additionally include a storage device 1516 (e.g., a drive unit), a signal generation device 1518 (e.g., a speaker), a network interface device 1520, and one or more sensors (not shown), such as a global positioning system (GPS) sensor, compass, accelerometer, or other sensor. It will be understood that other forms of machines or apparatuses (such as PIG, RC, CP devices, and the like) that are capable of implementing the methodologies discussed in this disclosure may not incorporate or utilize every component depicted in FIG. 15 (such as a GPU, video display unit, keyboard, etc.).

The storage device 1516 includes a machine-readable medium 1522 on which is stored one or more sets of data structures and instructions 1524 (e.g., software) embodying or utilized by any one or more of the methodologies or functions described herein. The instructions 1524 may also reside, completely or at least partially, within the main memory 1504, static memory 1506, and/or within the processor 1502 during execution thereof by the computer system 1500, with the main memory 1504, static memory 1506, and the processor 1502 also constituting machine-readable media.

While the machine-readable medium 1522 is illustrated in an example embodiment to be a single medium, the term "machine-readable medium" may include a single medium or multiple media (e.g., a centralized or distributed database, and/or associated caches and servers) that store the one or more instructions 1524. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EE-PROM)) and flash memory devices; magnetic disks such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A device for use to evaluate a neurostimulation treatment provided from a neurostimulation device, the device comprising:

at least one processor and at least one memory;

data processing circuitry, operable with the processor and the memory, the data processing circuitry configured to:

receive device data from the neurostimulation device, the neurostimulation device being used for neurostimulation treatment of a human patient; and identify a state of the neurostimulation treatment of the human patient from the device data;

text processing circuitry, operable with the processor and the memory, the text processing circuitry configured to:

receive text content relating to a state of the human patient, the text content originating from input of the human patient; and identify a state of the human patient from natural language processing of the text content, wherein the state of the human patient is determined from identifying a sentiment of at least one statement provided in the text content using the natural language processing, and wherein the sentiment of the at least one statement comprises a calculated sentiment value that is compared with a threshold sentiment value; and neurostimulation treatment evaluation circuitry, in operation with the at least one processor and the at least one memory, configured to:

associate the identified state of the human patient with the identified state of the neurostimulation treatment; and initiate an action for the neurostimulation treatment, based on the identified state of the human patient that is associated with the identified state of the neurostimulation treatment, wherein the action for the neurostimulation treatment causes a change to a neurostimulation programming setting on the neurostimulation device that delivers the neurostimulation treatment to the human patient, and wherein the action for the neurostimulation treatment is initiated based on the calculated sentiment value exceeding the threshold sentiment value.

2. The device of claim 1, wherein the calculated sentiment value is produced from a negative sentiment value, a neutral sentiment value, and a positive sentiment value that is calculated for each of the at least one statement.

3. The device of claim 1, wherein the state of the human patient comprises at least one physiological condition identified using the natural language processing, wherein the at least one physiological condition relates to: pain, sleep, movement, medication, or emotional state, of the human patient, and wherein the state of the neurostimulation treatment comprises at least one device condition identified from the device data, wherein the at least one device condition relates to: power status, program usage, battery level, impedance, device settings, or scheduled cycles, for the neurostimulation device.

4. The device of claim 1, wherein operations to associate the identified state of the human patient to the identified state of the neurostimulation treatment comprise operations to:

match use of at least one neurostimulation program to the identified state of the human patient, the at least one neurostimulation program used by the neurostimulation device.

5. The device of claim 4, wherein the use of the at least one neurostimulation program is identified based on a time of the use of the at least one neurostimulation program, matched to at least one time associated with the identified state of the human patient.

6. The device of claim 1, wherein the text content originates from at least one of:

a text chat session conducted between a chatbot and the human patient;

a voice chat session conducted between a virtual agent and the human patient, with at least a portion of the voice chat session converted to text;

a text message session conducted between a text service and the human patient;

an audio recording of a discussion conducted between the human patient and a human agent, with at least a portion of the audio recording converted to text; or a freeform text input provided by the human patient.

7. The device of claim 1, wherein the initiated action comprises operations to:

provide an alert to a clinician or a customer assistance entity associated with the neurostimulation treatment of the human patient, the alert to provide information for the identified state of the human patient and the identified state of the neurostimulation treatment;

perform a diagnostic action on the neurostimulation device; or provide activity, behavior, or therapy recommendations to the human patient.

8. The device of claim 1, wherein the change to the neurostimulation programming setting comprises operations to identify programming values for at least one neurostimulation programming parameter in the neurostimulation program based on the identified state of the human patient that is associated with the identified state of the neurostimulation treatment; and wherein the identified programming values specify a change in operation of the neurostimulation program for one or more of: pulse patterns, pulse shapes, a spatial location of pulses, waveform shapes, or a spatial location of waveform shapes, for modulated energy provided with a plurality of leads of the neurostimulation device.

9. A method for use to evaluate a neurostimulation treatment provided from a neurostimulation device, the method comprising a plurality of operations executed with at least one processor of an electronic device, the plurality of operations comprising:

obtaining text content relating to a state of a human patient, the text content originating from input of the human patient;

identifying a state of the human patient from natural language processing of the text content, wherein the state of the human patient is determined from identifying a sentiment of at least one statement provided in the text content using the natural language processing, and wherein the sentiment of the at least one statement comprises a calculated sentiment value that is compared with a threshold sentiment value;

obtaining device data from the neurostimulation device, the neurostimulation device being used for neurostimulation treatment of the human patient;

identifying a state of the neurostimulation treatment of the human patient from the device data;

associating the identified state of the human patient with the identified state of the neurostimulation treatment; and initiating an action for the neurostimulation treatment, based on the identified state of the human patient that is associated with the identified state of the neurostimulation treatment, wherein the action for the neurostimulation treatment causes a change to a neurostimulation programming setting on the neurostimulation device that delivers the neurostimulation treatment to the human patient, and wherein the action for the neurostimulation treatment is initiated based on the calculated sentiment value exceeding the threshold sentiment value.

10. The method of claim 9, wherein the calculated sentiment value is produced from a negative sentiment value, a neutral sentiment value, and a positive sentiment value that is calculated for each of the at least one statement.

11. The method of claim 9, wherein the state of the human patient comprises at least one physiological condition identified using the natural language processing, wherein the at least one physiological condition relates to: pain, sleep, movement, medication, or emotional state, of the human patient, and wherein the state of the neurostimulation treatment comprises at least one device condition identified from the device data, wherein the at least one device condition relates to: power status, program usage, battery level, impedance, device settings, or scheduled cycles, for the neurostimulation device.

12. The method of claim 9, wherein associating the identified state of the human patient to the identified state of the neurostimulation treatment comprises:

matching use of at least one neurostimulation program to the identified state of the human patient, the at least one neurostimulation program used by the neurostimulation device.

13. The method of claim 12, wherein the use of the at least one neurostimulation program is identified based on a time of the use of the at least one neurostimulation program, matched to at least one time associated with the identified state of the human patient.

14. The method of claim 9, wherein the text content originates from at least one of:

a text chat session conducted between a chatbot and the human patient;

a voice chat session conducted between a virtual agent and the human patient, with at least a portion of the voice chat session converted to text;

a text message session conducted between a text service and the human patient;

an audio recording of a discussion conducted between the human patient and a human agent, with at least a portion of the audio recording converted to text; or a freeform text input provided by the human patient.

15. The method of claim 9, wherein the initiated action comprises:

providing an alert to a clinician or a customer assistance entity associated with the neurostimulation treatment of the human patient, the alert to provide information for the identified state of the human patient and the identified state of the neurostimulation treatment;

performing a diagnostic action on the neurostimulation device; or providing activity, behavior, or therapy recommendations to the human patient.

16. The method of claim 9, wherein the change to the neurostimulation programming setting comprises identifying programming values for at least one neurostimulation programming parameter in the neurostimulation program based on the identified state of the human patient that is associated with the identified state of the neurostimulation treatment; and wherein the identified programming values specify a change in operation of the neurostimulation program for one or more of: pulse patterns, pulse shapes, a spatial location of pulses, waveform shapes, or a spatial location of waveform shapes, for modulated energy provided with a plurality of leads of the neurostimulation device.

* * * * *